United States Patent
Tripathi et al.

(10) Patent No.: US 10,019,819 B2
(45) Date of Patent: *Jul. 10, 2018

(54) IMAGING SYSTEM AND METHODS DISPLAYING A FUSED MULTIDIMENSIONAL RECONSTRUCTED IMAGE

(71) Applicant: TrueVision Systems, Inc., Santa Barbara, CA (US)

(72) Inventors: Ashok Burton Tripathi, Santa Barbara, CA (US); George Charles Polchin, Santa Barbara, CA (US); Yen Ting Ng, Goleta, CA (US)

(73) Assignee: TrueVision Systems, Inc., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/412,959

(22) Filed: Jan. 23, 2017

(65) Prior Publication Data
US 2017/0132812 A1  May 11, 2017

Related U.S. Application Data

(63) Continuation of application No. 14/424,985, filed as application No. PCT/US2013/057686 on Aug. 30, 2013, now Pat. No. 9,552,660.
(Continued)

(51) Int. Cl.
*G06K 9/00* (2006.01)
*G06T 11/00* (2006.01)
(Continued)

(52) U.S. Cl.
CPC .......... *G06T 11/008* (2013.01); *A61B 5/0077* (2013.01); *A61B 5/055* (2013.01);
(Continued)

(58) Field of Classification Search
None
See application file for complete search history.

(56) References Cited

U.S. PATENT DOCUMENTS 3,431,992 A  3/1969  Whitecar
3,517,183 A  6/1970  Rebres
(Continued)

FOREIGN PATENT DOCUMENTS

DE  3431992  4/1985
JP  3209543  9/1991
(Continued)

OTHER PUBLICATIONS

US 3,973,836, 08/1976, Govignon et al. (withdrawn)
(Continued)

*Primary Examiner* — Hadi Akhavannik
(74) *Attorney, Agent, or Firm* — K&L Gates LLP; Louis C. Cullman; Dennis A. Majewski

(57) ABSTRACT

A system, method, and apparatus for displaying a fused reconstructed image with a multidimensional image are disclosed. An example imaging system receives a selection corresponding to a portion of a displayed multidimensional visualization of a surgical site. At the selected portion of the multidimensional visualization, the imaging system displays a portion of a reconstructed image which corresponds to the selected multidimensional visualization such that the displayed portion of the reconstructed image is fused with the displayed multidimensional visualization.

20 Claims, 9 Drawing Sheets

Related U.S. Application Data

(60) Provisional application No. 61/695,230, filed on Aug. 30, 2012.

(51) Int. Cl.

| | | |
|---|---|---|
| *G06T 19/00* | (2011.01) | |
| *A61B 5/00* | (2006.01) | |
| *A61B 5/055* | (2006.01) | |
| *A61B 6/03* | (2006.01) | |
| *G06K 9/20* | (2006.01) | |
| *G06T 7/00* | (2017.01) | |
| *G06T 19/20* | (2011.01) | |
| *A61B 90/20* | (2016.01) | |
| *A61B 90/00* | (2016.01) | |
| *G06T 7/33* | (2017.01) | |
| *G06K 9/46* | (2006.01) | |
| *G06T 5/00* | (2006.01) | |
| *H04N 13/02* | (2006.01) | |
| *H04N 13/04* | (2006.01) | |
| *G06F 19/00* | (2018.01) | |

(52) U.S. Cl.
CPC .............. *A61B 5/743* (2013.01); *A61B 5/745* (2013.01); *A61B 5/7425* (2013.01); *A61B 6/03* (2013.01); *A61B 6/032* (2013.01); *A61B 6/037* (2013.01); *A61B 90/20* (2016.02); *A61B 90/37* (2016.02); *G06F 19/321* (2013.01); *G06K 9/2081* (2013.01); *G06K 9/4604* (2013.01); *G06T 5/002* (2013.01); *G06T 7/0014* (2013.01); *G06T 7/337* (2017.01); *G06T 19/00* (2013.01); *G06T 19/20* (2013.01); *H04N 13/0203* (2013.01); *H04N 13/04* (2013.01); *A61B 2090/365* (2016.02); *A61B 2090/3983* (2016.02); *A61B 2576/00* (2013.01); *G06T 2200/24* (2013.01); *G06T 2207/10021* (2013.01); *G06T 2207/10028* (2013.01); *G06T 2207/10088* (2013.01); *G06T 2207/20104* (2013.01); *G06T 2207/20221* (2013.01); *G06T 2207/30016* (2013.01); *G06T 2207/30196* (2013.01); *G06T 2207/30204* (2013.01); *G06T 2210/41* (2013.01); *G06T 2210/62* (2013.01); *G06T 2211/40* (2013.01); *G06T 2219/028* (2013.01); *G06T 2219/2004* (2013.01)

(56) References Cited

U.S. PATENT DOCUMENTS

| | | |
|---|---|---|
| 3,867,697 A | 2/1975 | Vanzetti et al. |
| 4,395,731 A | 7/1983 | Schoolman |
| 4,691,997 A | 9/1987 | Munchel |
| 4,786,155 A | 11/1988 | Fantone et al. |
| 4,790,305 A | 12/1988 | Zoltan |
| 4,791,478 A | 12/1988 | Tredwell et al. |
| 4,967,268 A | 10/1990 | Lipton et al. |
| 4,989,078 A | 1/1991 | Paxton |
| 4,995,716 A | 2/1991 | Warnicki et al. |
| 5,007,715 A | 4/1991 | Verhhulst |
| 5,022,744 A | 6/1991 | Leiter |
| 5,045,936 A | 9/1991 | Lobb et al. |
| 5,048,946 A | 9/1991 | Sklar et al. |
| 5,054,907 A | 10/1991 | Sklar et al. |
| 5,098,426 A | 3/1992 | Sklar et al. |
| 5,109,276 A | 4/1992 | Nudelman et al. |
| 5,193,000 A | 3/1993 | Lipton et al. |
| 5,200,838 A | 4/1993 | Nudelman et al. |
| 5,513,005 A | 4/1996 | Muller et al. |
| 5,530,494 A | 6/1996 | Ogawa et al. |
| 5,545,120 A | 8/1996 | Chen et al. |
| 5,548,355 A | 8/1996 | Iki |
| 5,568,188 A | 10/1996 | Widmer et al. |
| 5,579,772 A | 12/1996 | Kinukawa et al. |
| 5,652,676 A | 7/1997 | Grinblat |
| 5,715,836 A | 2/1998 | Kliegis et al. |
| 5,740,802 A | 4/1998 | Nafis et al. |
| 5,751,927 A | 5/1998 | Wason |
| 5,815,240 A | 9/1998 | Iki |
| 5,825,532 A | 10/1998 | Mochizuki et al. |
| 5,835,133 A | 11/1998 | Moreton et al. |
| 5,867,210 A | 2/1999 | Rod |
| 5,867,309 A | 2/1999 | Spink |
| 5,870,137 A | 2/1999 | Stuettler |
| 5,873,822 A | 2/1999 | Ferre et al. |
| 5,912,763 A | 6/1999 | Spink et al. |
| 5,933,513 A | 8/1999 | Yoneyama et al. |
| 5,999,840 A | 12/1999 | Grimson et al. |
| 6,006,126 A | 12/1999 | Cosman |
| 6,069,733 A | 5/2000 | Spink et al. |
| 6,088,470 A | 7/2000 | Camus et al. |
| 6,133,762 A | 10/2000 | Hill et al. |
| 6,133,945 A | 10/2000 | Stuettler |
| 6,144,762 A | 11/2000 | Brooks |
| 6,147,797 A | 11/2000 | Lee |
| 6,179,421 B1 | 1/2001 | Pang |
| 6,191,809 B1 | 2/2001 | Hori et al. |
| 6,201,984 B1 | 3/2001 | Funda et al. |
| 6,241,672 B1 | 6/2001 | Hochman et al. |
| 6,256,529 B1 | 7/2001 | Holupka et al. |
| 6,276,799 B1 | 8/2001 | Van Saarloos et al. |
| 6,318,860 B1 | 11/2001 | Suzumura |
| 6,337,765 B1 | 1/2002 | Spink et al. |
| 6,396,627 B1 | 5/2002 | Tachihara et al. |
| 6,441,958 B1 | 8/2002 | Yeung et al. |
| 6,483,948 B1 | 11/2002 | Spink et al. |
| 6,522,906 B1 | 2/2003 | Salisbury, Jr. et al. |
| 6,596,025 B2 | 7/2003 | Portney |
| 6,607,527 B1 | 8/2003 | Ruiz et al. |
| 6,631,990 B2 | 10/2003 | Schippert et al. |
| RE38,307 E | 11/2003 | Gustafsson et al. |
| 6,643,070 B2 | 11/2003 | Deverin et al. |
| 6,675,032 B2 | 1/2004 | Chen et al. |
| 6,685,317 B2 | 2/2004 | Su et al. |
| 6,697,664 B2 | 2/2004 | Kienzle, III et al. |
| 6,765,718 B1 | 7/2004 | Spink et al. |
| 7,025,459 B2 | 4/2006 | Cornsweet et al. |
| 7,066,928 B2 | 6/2006 | Dick et al. |
| 7,110,614 B2 | 9/2006 | Launay et al. |
| 7,146,983 B1 | 12/2006 | Hohla et al. |
| 7,261,415 B2 | 8/2007 | Chernyak |
| 7,313,430 B2 | 12/2007 | Urquhart |
| 7,320,685 B2 | 1/2008 | Feige et al. |
| 7,331,667 B2 | 2/2008 | Grotehusmann et al. |
| 7,370,965 B2 | 5/2008 | Kojima et al. |
| 7,428,001 B2 | 9/2008 | Schowengerdt et al. |
| 7,431,457 B2 | 10/2008 | Chernyak |
| 7,654,668 B2 | 2/2010 | Neuhann et al. |
| 7,695,136 B2 | 4/2010 | Dai |
| 7,831,096 B2 | 11/2010 | Williamson, Jr. |
| 7,905,887 B2 | 3/2011 | Moeller et al. |
| 7,959,289 B2 | 6/2011 | Cattin-Liebl |
| 8,025,400 B2 | 9/2011 | Chernyak |
| 8,057,038 B2 | 11/2011 | Dai et al. |
| 8,088,124 B2 | 1/2012 | Loesel et al. |
| 8,131,343 B2 | 3/2012 | Burgkart |
| 8,186,830 B2 | 5/2012 | Grotehusmann et al. |
| 8,192,445 B2 | 6/2012 | Parmer et al. |
| 8,375,956 B2 | 2/2013 | Gray et al. |
| 8,414,123 B2 | 4/2013 | Boukhny et al. |
| 8,454,160 B2 | 6/2013 | Dai |
| 8,474,974 B2 | 7/2013 | Dai |
| 8,486,085 B2 | 7/2013 | Moeller et al. |
| 8,528,566 B2 | 9/2013 | Loesel et al. |
| 8,708,488 B2 | 4/2014 | Kraus |
| 8,740,385 B2 | 6/2014 | Chernyak |
| 8,784,443 B2 | 7/2014 | Tripathi |
| 8,848,869 B2 | 9/2014 | Gertner et al. |
| 8,978,660 B2 | 3/2015 | Chernyak et al. |
| 2002/0063850 A1 | 5/2002 | Barry et al. |
| 2002/0080478 A1 | 6/2002 | Manns |

(56) References Cited

U.S. PATENT DOCUMENTS

| | | |
|---|---|---|
| 2002/0097378 A1 | 7/2002 | Saito et al. |
| 2002/0156345 A1 | 10/2002 | Eppler |
| 2003/0021016 A1 | 1/2003 | Grier |
| 2003/0053025 A1 | 3/2003 | Turner et al. |
| 2003/0055410 A1 | 3/2003 | Evans et al. |
| 2003/0071893 A1 | 4/2003 | Miller et al. |
| 2003/0120266 A1 | 6/2003 | Fujieda |
| 2003/0142271 A1* | 7/2003 | Ross et al. |
| 2003/0184855 A1 | 10/2003 | Yasuda et al. |
| 2003/0185450 A1 | 10/2003 | Garakani et al. |
| 2003/0223037 A1 | 12/2003 | Chernyak |
| 2004/0017607 A1 | 1/2004 | Hauger et al. |
| 2004/0227828 A1 | 11/2004 | Loose |
| 2004/0252276 A1 | 12/2004 | Nanjo et al. |
| 2004/0263785 A1 | 12/2004 | Chernyak |
| 2004/0264765 A1 | 12/2004 | Ohba |
| 2005/0007659 A1 | 1/2005 | Steinthal et al. |
| 2005/0014996 A1 | 1/2005 | Konomura et al. |
| 2005/0018135 A1 | 1/2005 | Maeda et al. |
| 2005/0024720 A1 | 2/2005 | Cartildge |
| 2005/0025365 A1 | 2/2005 | Oosawa |
| 2005/0046930 A1 | 3/2005 | Olschewski |
| 2005/0071087 A1 | 3/2005 | Anderson |
| 2005/0107808 A1 | 5/2005 | Evans et al. |
| 2005/0111088 A1 | 5/2005 | Winterot et al. |
| 2005/0117118 A1 | 6/2005 | Miller et al. |
| 2005/0128573 A1 | 6/2005 | Merz |
| 2005/0200808 A1 | 9/2005 | Wyatt |
| 2005/0203384 A1 | 9/2005 | Sati et al. |
| 2005/0225721 A1 | 10/2005 | Harris et al. |
| 2006/0084955 A1 | 4/2006 | Hindi et al. |
| 2006/0116668 A1 | 6/2006 | Gray et al. |
| 2006/0223037 A1 | 10/2006 | Tanda |
| 2007/0081709 A1* | 4/2007 | Warmath ............ G09B 23/285 |
| | | 382/128 |
| 2007/0121202 A1 | 5/2007 | Riederer |
| 2007/0121203 A1 | 5/2007 | Riederer |
| 2007/0188603 A1 | 8/2007 | Riderer |
| 2008/0018643 A1* | 1/2008 | Feilkas ..................... G06T 7/50 |
| | | 345/420 |
| 2008/0103367 A1 | 5/2008 | Burba et al. |
| 2008/0118115 A1 | 5/2008 | Williamson |
| 2008/0247616 A1 | 10/2008 | Pescatore et al. |
| 2009/0048608 A1 | 2/2009 | Boukhny et al. |
| 2009/0125088 A1 | 5/2009 | Schleicher et al. |
| 2009/0137988 A1 | 5/2009 | Kurtz |
| 2009/0143772 A1 | 6/2009 | Kurtz |
| 2009/0171358 A1 | 7/2009 | Chang et al. |
| 2009/0236541 A1 | 9/2009 | Lomnes et al. |
| 2009/0254070 A1 | 10/2009 | Tripathi |
| 2010/0045933 A1 | 2/2010 | Eberl et al. |
| 2010/0094262 A1 | 4/2010 | Tripathi |
| 2010/0208199 A1 | 8/2010 | Levis et al. |
| 2010/0217278 A1 | 8/2010 | Tripathi |
| 2011/0064286 A1 | 3/2011 | Chien et al. |
| 2011/0102549 A1 | 5/2011 | Takahashi |
| 2011/0160578 A1 | 6/2011 | Tripathi |
| 2011/0202046 A1 | 8/2011 | Angeley et al. |
| 2011/0213342 A1 | 9/2011 | Tripathi |
| 2011/0224657 A1 | 9/2011 | Stevens et al. |
| 2011/0274322 A1 | 11/2011 | Kern et al. |
| 2011/0286630 A1 | 11/2011 | Harder et al. |
| 2012/0172854 A1 | 7/2012 | Raymond et al. |
| 2012/0242956 A1 | 9/2012 | Chernyak |
| 2014/0114297 A1 | 4/2014 | Woodley et al. |
| 2014/0125949 A1 | 5/2014 | Shea et al. |
| 2014/0257258 A1 | 9/2014 | Kurtz |
| 2014/0303486 A1 | 10/2014 | Baumgartner et al. |
| 2014/0316388 A1 | 10/2014 | Hipsley |
| 2014/0324071 A1 | 10/2014 | Tripathi |
| 2016/0038337 A1 | 2/2016 | Tripathi |
| 2016/0051360 A1 | 2/2016 | Tripathi |

FOREIGN PATENT DOCUMENTS

| | | |
|---|---|---|
| JP | 2009-061035 | 3/2009 |
| WO | 2000/060992 | 10/2000 |
| WO | 2000/060998 | 10/2000 |
| WO | 2003/030763 | 4/2003 |
| WO | 2005/000139 A1 | 1/2005 |
| WO | 2005042760 | 5/2005 |
| WO | 2009/158517 A3 | 12/2009 |

OTHER PUBLICATIONS

Gering et al., An integrated visualization system for surgical planning and guidance using image fusion and interventional imaging. Medical Image Computing and Computer Assisted Intervention—Miccai '99. Second International Conference, Cambridge, UK, Sep. 19-22, 1999, pp. 809-819.

Supplementary European Search Report for European Patent Application 13834045 dated Jul. 14, 2017.

"Eye Surgery Using 3D Technology," WSFL video clip, <URL: http://southflorida.sun sentinel.com/videobeta/watch/?watch=d69be520-0d51-4a4d-b2d2-d27f20f4bfcc&cat=empty &src=front&title=Eye%20surgery%20using%203D %20technology/.

Canrobert Oliveira, MD, The 'Keratopyramis Phenomenum' and The Canrobert 'C' Procedure, International Society of Refractive Keratoplasty 193 Pre-American Academy of Ophthalmology, Nov. 12, 1993 and Nov. 13, 1993 Chicago, Illinois USA.

DentiMag3D. Product Description [online]. StereoImaging Corporation [retrieved on Oct. 13, 2005]. retrieved from the Internet: <URL:http://www.stereoimaging.com/products/dentimag.html>.

Edward J. Holland, MD, Acrysof Toric IOL: Surgical Pearls, Cataract & Refractive Surgery Today, May 2006, pp. 71-72.

International Search Report for PCT/US2011/025746.

James P. Gills, MD, Nomogram for Limbal Relaxing Incisions with Cataract Surgery.

John Chang, M.D., Cyclotorsion during laser in situ keratomileusis, J. Cataract Refract Surg, 34:1720-1726 (2008).

Leica IC 3D. product Description [online]. Leica Microsystems [retrived on Oct. 13, 2005]. Retrieved from the Internet: <URL: http://www.oleica-microsystems.com/website/lms.nsf?opendatabase&path=/website/products.nsf/(ALLIDs)/ECFFFC6CF17470FEC125706D002FBF06>.

Leica ICD: compact, Integrated Digital Camera for stereomiroscopes. Brochure [online]. Leica Microsystems, 2005, pp. 1-4 [retrieved on Apr. 20, 2006]. Retrieved from the Internet:<URL:http://www.leica-microsystems.com/website/lms.nsf?opendatabase&path=/WebSite/Download.nsf/(ALLIDs)/1C611440E77FF0EFC125700B003E478C>.

Louis D. "Skip" Nichamin, MD, Management of Astigmatism at the Time of Lens-Based Surgery, Tasman W. Jaeger E.A., Duane's Clinical Ophthalmology, 2006 Edition.

Posted by RCJONES, Bascom Palmer Eye Institute again ranked nation's No. 1 eye hospital by U.S. News & World Report, Jul. 17, 2009, <URL: http://everitas.univmiami.net/2009/07/17/bascom-palmer-eye-institute-again-rankednations-no-1-eye-hospital-by-us-news-world-report/.

Retrieved on Aug. 27, 2008 . retrieved from the Internet, <URL:http://www.LRIcalculator.com.

Robert J. Weinstock, MD, Heads Up Cataract Surgery Using the Truevision 3D System.

Ron Rajecki, The future of cataract surgery: Improved ergonomics, Ophthalmology Times, Jul. 1, 2009.

Rupert Menapace, MD, Posterior Capsulorrhexis and Optic Buttoning-In Combined with Anterior Capsule Polishing, Cataract & Refractive Surgery Today Europe, Jan./Feb. 2008, pp. 16-19.

Stephen Nellis, Venture capital in a freeze—But Santa Barbara med-tech company isn't giving up, Pacific Coast Business Times, Jan. 25, 2009.

Suenaga et al., Real-time in situ three-dimensional integral videography and surgical navigation using augmented reality: a pilot study. International Journal of Oral Science 5: 98-102 (2013).

(56) References Cited

OTHER PUBLICATIONS

Technology to perform LRIs using lasers [online]. LensAR Inc. [retrieved on Oct. 20, 2009]. retrieved from the Internet, <URL:http://www.sujanani.com/lasik/lasik_surgery/?p=101859.

Technology to perform LRIs using lasers [online]. LenSx Lasers, Inc. [retrieved on Oct. 20, 2009]. retrieved from the Internet, <URL:http://www.ventureinvestors.com/archives/1516.

Technology to perform LRIs using lasers [online]. OptiMedica [retrieved on Oct. 20, 2009]. retrieved from the Internet, <URL:http://www.optimedica.com/.

The World's Only: Interactive Leica 3D System for Microscopy. Press Release [online]. Leica Microsystems, Jun. 24, 2005, pp. 1-2 [retrieved on Oct. 13, 2005]. Retrieved from the Internet: <URL:http://www.leica-microsystems.com/website/lms.nsf?opendatabase&path=/website/products.nsf/(ALLIDs)/ECFFFcCF17470FEC125706D002FBF06> (See Press Releases).

TrueVision Systems Inc., 510K Application Summary for TrueVision 3D Visualization and Guidance System, Dec. 22, 2010.

U.S. Office Action mailed by Office on Mar. 29, 2016 for U.S. Appl. No. 13/024,948, filed Feb. 10, 2011.

International Search Report for PCT/US2013/057686 dated Mar. 6, 2014.

\* cited by examiner

IMAGING SYSTEM AND METHODS DISPLAYING A FUSED MULTIDIMENSIONAL RECONSTRUCTED IMAGE

PRIORITY CLAIM

The present application is a continuation of and claims priority to and the benefit of U.S. patent application Ser. No. 14/424,985, now U.S. Pat. No. 9,552,660, filed on Feb. 27, 2015, which claims priority to and the benefit of PCT Patent Application No. PCT/US2013/057686, filed on Aug. 30, 2013, which claims priority to and the benefit of U.S. Provisional Patent Application No. 61/695,230, filed on Aug. 30, 2012, the entirety of which are incorporated herein by reference.

BACKGROUND

Brain and other organ surgery involve complex surgical procedures to access intricate and delicate portions of tissue. Oftentimes, surgeons will image areas of a patient's body where the surgery is to be performed. These images help surgeons plan how the surgery is to be performed, identify specific areas of tissue that need to be accessed, and determine pathways through the body for surgical tools and cameras to access the target tissue.

In a typical surgery, surgeons will generally first image an area of a patient where the surgery is to be performed. Surgeons will meticulously review these images to plan how the surgery is to be preformed. Even during surgery, surgeons may again review physical copies of these images or access a video monitor and scroll through the images as a way to refresh their memory or to help determine their bearings. An issue with this procedure is that it requires surgeons to look at the surgical site, then direct their attention to a video monitor or physical images, and then redirect their attention back to the patient. In other words, the surgeons have to mentally relate the images to the anatomy of the patient.

This diversion of attention between patient and images may be mentally taxing on a surgeon during a relatively long surgery. This may also extend the length of a surgery if a surgeon has to refer to the images many times. Further, this may be especially tricky and time consuming for a surgeon when an orientation of the images does not match up to the surgeon's current view of the patient. For instance, a set of images of an MRI scan of a patient's head may include hundreds of individual images layered in a straight and level orientation. A surgeon looking down at the top of the patient's head to determine where to make an incision to reach a deeply embedded tumor has to construct and rectify in his mind: (1) the different layers of MRI images between the top of the head and the level of the tumor, (2) the orientation of the MRI images versus the orientation of the patient, and (3) the specific location on the MM images as corresponding to an actual location on the patient.

To increase the accuracy of incisions made during surgery and to decrease the amount of surgery time, it is desirable to provide surgeons with new types of imaging systems. Accordingly, a need exits for further development of imaging systems.

SUMMARY

In some embodiments, the imaging systems, imaging apparatuses and imaging methods fuse portions of a multi-dimensional reconstructed image with multidimensional visualizations of at least a portion of a surgical site. The imaging systems may generate multidimensional reconstructed images based on pre-operative image data. At a selected portion of the visualization, the imaging systems may display a portion of the multidimensional reconstructed image.

In some embodiments, imaging systems display a window through a live surgery visualization into a multidimensional reconstructed image below a surface of at least a portion of a surgical site. Such a configuration may be referred to as providing "x-ray vision" window capability.

In some embodiments, imaging systems enable users to control the window to suit their immediate needs. For example, using a mouse, joystick, foot pedal, or any other suitable control device, imaging systems may enable a user to control the window in x, y, and z directions. Such control devices also may enable a user to control the orientation of the displayed portion of the multidimensional reconstructed image. For example, imaging systems may enable the user to control the orientations via a yaw button, pitch button and roll button. Still further, imaging systems may enable a user to control the scale or transparency of the displayed multidimensional reconstructed image.

The window may have any suitable shape. The window may be round, square, rectangular, elliptical, or any other geometric shape. In some embodiments, the window may also have an anatomical shape (e.g., the window may follow the outline of a tumor or organ). In some embodiments, the window is fused or blended with the live multidimensional visualization at the edges using a fading level of transparency (e.g., alpha blending). In some embodiments, the overall window itself may be alpha blended with the live multidimensional visualization using adjustable transparency.

In some embodiments, imaging systems enable a user to adjust the window position and shape. In some embodiments, the imaging system may algorithmically drive the imaging system to follow notations or highlighted anatomy throughout the course of a surgical procedure.

Additional features and advantages are described herein and will be apparent from the following Detailed Description and the figures.

DETAILED DESCRIPTION

The present disclosure relates in general to systems for displaying a portion of a multidimensional image at a selected portion of a visualization of a surgical site. Imaging systems enable user(s) to select the portion of the visualization in which a portion of a multidimensional reconstructed image is displayed.

Figure 1:
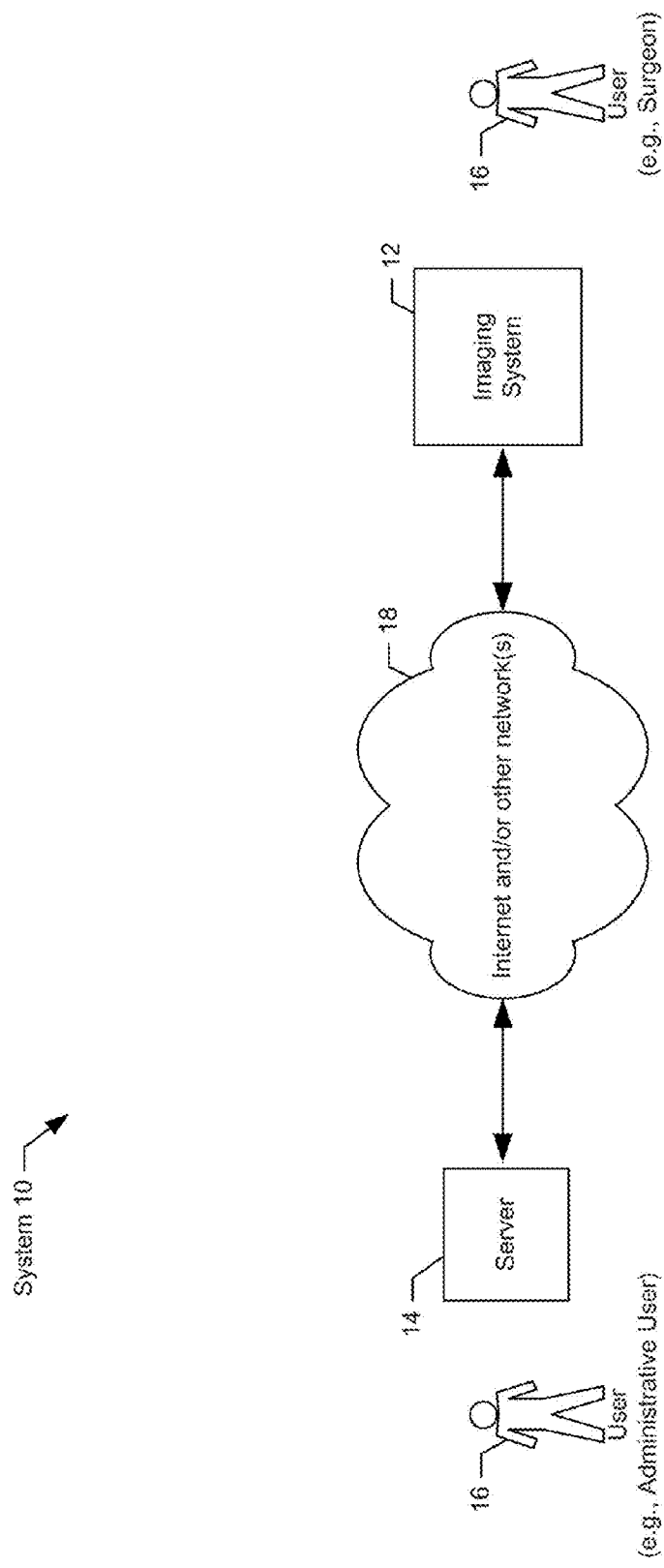
FIG. 1 is a block diagram of an example network communicating system, according to an example embodiment of the system disclosed herein.

The imaging systems described herein may be readily realized in a network communications system. A block diagram of an example network communications system 10 ("system 10") is illustrated in FIG. 1. In this example, system 10 includes an imaging system 12 and server 14.

It should be appreciated that users as described herein may include any person or entity which uses the presently disclosed system and may include a wide variety of parties. For example, reference is made herein to surgeons operating surgical equipment including the exemplary imaging systems. It should be appreciated that the exemplary imaging system may be used by anyone including nurses, surgical assistants, veterinary personnel, autopsy technicians, medical students, surgical residents, the surgeon's staff or anyone else who is to view a portion of a multidimensional reconstructed image being fused with a visualization of a surgical site.

Imaging system 12 and/or server 14 may be configured according to its particular operating system, applications, memory, hardware, etc., and may provide various options for managing the execution of the programs and applications, as well as various administrative tasks. Imaging system 12 and/or server 14 may interact via at least one network with at least one other imaging system 12 and/or server 14, which may be operated independently. Information processing systems 12 and servers 14 operated by separate and distinct entities may interact together according to some agreed upon protocol.

Figure 2:
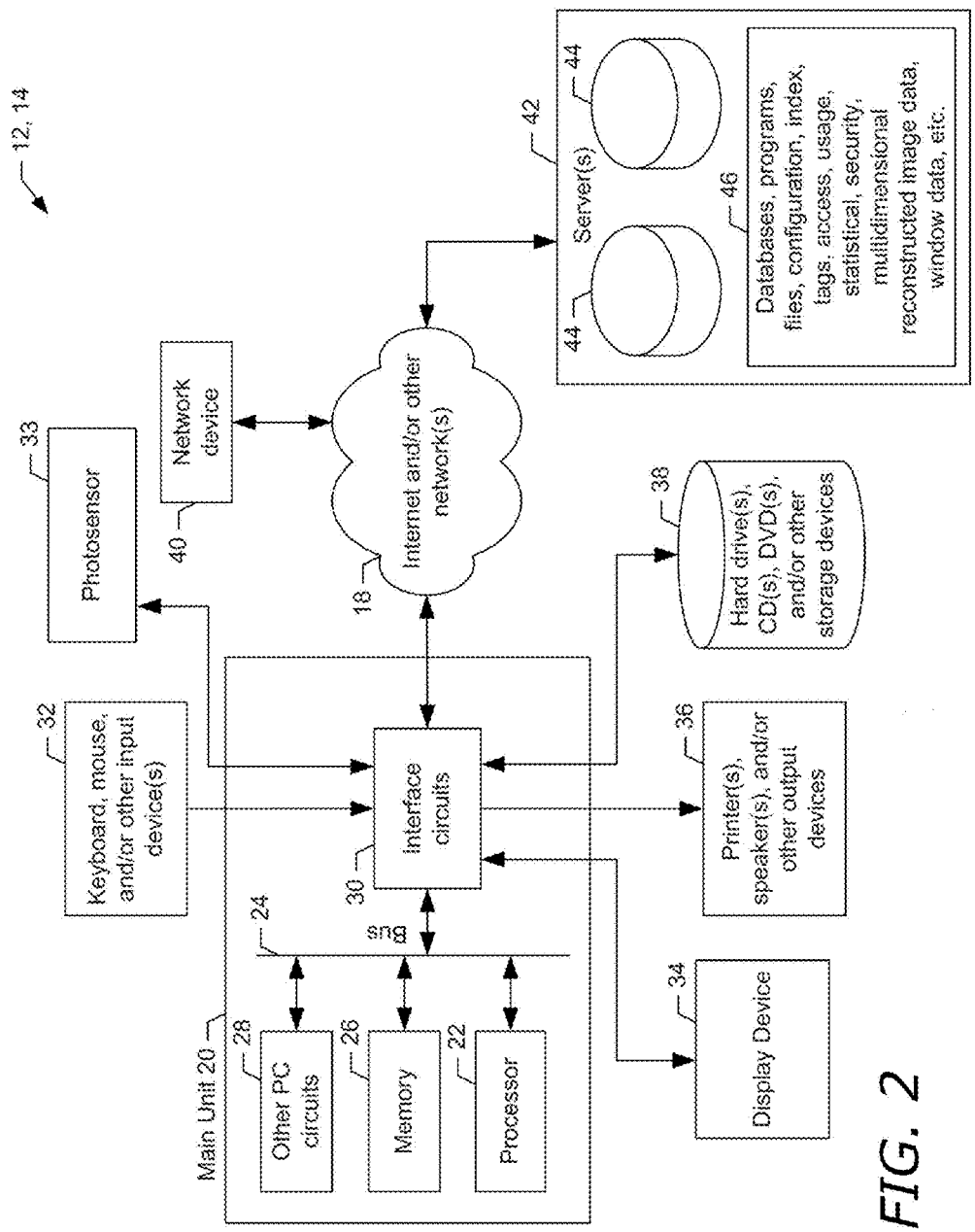
FIG. 2 is a block diagram showing an example of a computing device, according to an example embodiment of the system disclosed herein.

A detailed block diagram of the electrical systems of an example computing device is illustrated in FIG. 2. The example computing device may include any of the devices and systems described herein, including imaging system 12 and server 14. In this example, the example computing devices may include main unit 20 which preferably includes at least one processor 22 electrically connected by address/data bus 24 to at least one memory device 26, other computer circuitry 28, and at least one interface circuit 30. Processor 22 may be any suitable processor, such as a microprocessor from the INTEL® CORE® family of microprocessors. Processor 22 may include one or more microprocessors, central processing units (CPUs), computing devices, microcontrollers, graphics processing units (GPUs), digital signal processors, or like devices or any combination thereof. Memory 26 preferably includes volatile memory and non-volatile memory. Preferably, memory 26 stores software program(s) or instructions that interact with the other devices in system 10 as described below. This program may be executed by processor 22 in any suitable manner. In an example embodiment, memory 26 may be part of a "cloud" such that cloud computing may be utilized by imaging system 12 and server 14. Memory 26 may also store digital data indicative of images, documents, files, programs, web pages, etc. retrieved from computing devices 12, 14 and/or loaded via input device 32.

Interface circuit 30 may be implemented using any suitable interface standard, such as an Ethernet interface and/or a Universal Serial Bus (USB) interface. At least one input device 32 may be connected to interface circuit 30 for entering data and commands into main unit 20. For example, input device 32 may be at least one of a keyboard, mouse, joystick, touch screen device, remote control, foot-pedal device, gesture recognition device, track pad, track ball, isopoint, character recognition, barcode scanner, and a voice recognition system. In one example embodiment, at least one input device 32 includes an image sensor and/or camera system, such as photosensor 33.

As illustrated in FIG. 2, at least one display device 34, printers, speakers, and/or other output devices 36 may also be connected to main unit 20 via interface circuit 30. Display device 34 may be any device capable of displaying a still or video image. Preferably, display device 34 displays high definition (HD) still images and video images or videos which provide a surgeon with a greater level of detail than a standard definition (SD) signal. More preferably, display device 34 is configured to display HD stills and images in three dimensions (3D). Exemplary display devices include HD monitors, cathode ray tubes, projection screens, liquid crystal displays, organic light emitting diode displays, plasma display panels, light emitting diodes, 3D equivalents thereof and the like. In some embodiments, display device 34 includes a 3D HD holographic display system. In one example embodiment, display device 34 is a projection cart display system and incorporates the basic structural components of the Applicant's TrueVision Systems, Inc. stereoscopic image display cart described in the Applicant's co-pending U.S. application Ser. No. 11/739,042, entitled "Stereoscopic Display Cart and System" filed Apr. 23, 2007, which is fully incorporated herein by reference as if part of this specification. For example, display device 34 may provide a user interface, which will be described in further detail below, and may display at least one web page received from imaging system 12 and/or server 14. A user interface may include prompts for human input from user 16 including links, buttons, tabs, checkboxes, thumbnails, text fields, drop down boxes, etc., and may provide various outputs in response to the user inputs, such as text, still images, videos, audio, and animations.

At least one storage device 38 may also be connected to main device or unit 20 via interface circuit 30. At least one storage device 38 may include at least one of a hard drive, CD drive, DVD drive, and other storage devices. At least one storage device 38 may store any type of data, such as multidimensional visualization data, multidimensional reconstructed image data, selection data, window data, image data, content data, statistical data, historical data, databases, programs, files, libraries, and/or other data, etc., which may be used by imaging system 12 and/or server 14.

Imaging system 12 and/or server 14 may also exchange data with other network devices 40 via a connection to network 18. Network devices 40 may include at least one server 42, which may be used to store certain types of data, and particularly large volumes of data which may be stored in at least one data repository 44. Server 42 may include any kind of data 46 including multidimensional visualization data, multidimensional reconstructed image data, selection data, window data, image data, content data, statistical data, historical data, databases, programs, files, libraries, and/or other data, etc. Server 42 may store and operate various applications relating to receiving, transmitting, processing, and storing the large volumes of data. It should be appreciated that various configurations of at least one server 42 may be used to support and maintain system 10. In some example embodiments, server 42 is operated by various different entities, including private individuals, administrative users and/or commercial partners. Also, certain data may be stored in imaging system 12 and/or server 14 which is also stored on server 42, either temporarily or permanently, for example in memory 26 or storage device 38. The network connection may be any type of network connection, such as an ethernet connection, digital subscriber line (DSL), telephone line, coaxial cable, wireless connection, etc.

Access to imaging system 12 and/or server 14 can be controlled by appropriate security software or security measures. A user's access can be denied to imaging system 12 and/or server 14 and be limited to certain data and/or actions. Accordingly, users of system 10 may be required to register with imaging system 12 and/or server 14.

As noted previously, various options for managing data located within imaging system 12, server 14 and/or in server 42 may be implemented. A management system may manage security of data and accomplish various tasks such as facilitating a data backup process. The management system may update, store, and back up data locally and/or remotely. A management system may remotely store data using any suitable method of data transmission, such as via the Internet and/or other networks 18.

Figure 3:
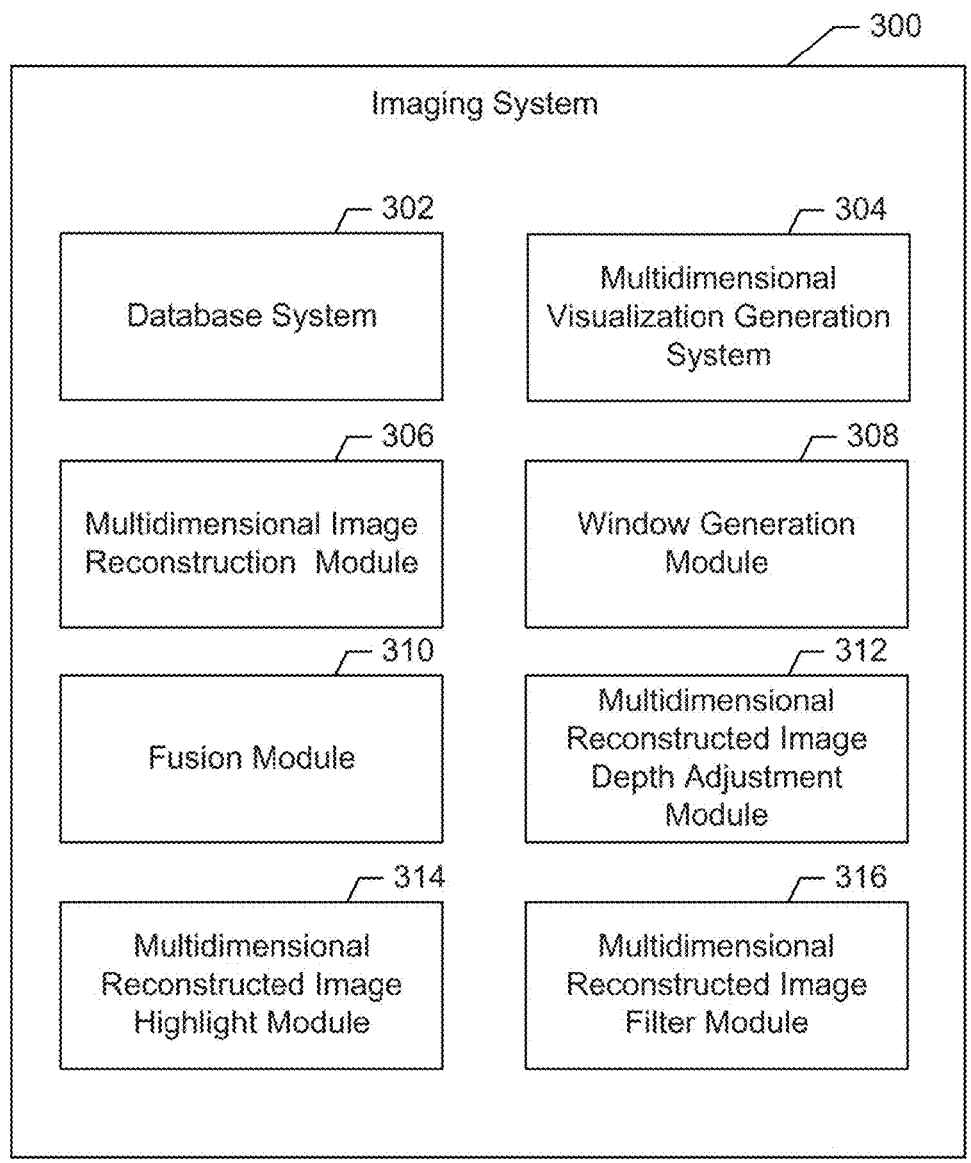
FIG. 3 is a block diagram of an example structure in accordance with an example embodiment of the imaging system disclosed herein.

FIG. 3 is a block diagram showing an example imaging system 300. Imaging system 300 is operated by a user such as a surgeon. It should be appreciated that imaging system 300 illustrated in FIG. 3 may be implemented as imaging system 12.

As illustrated in FIG. 3, in this example, imaging system 300 includes database system 302, multidimensional visualization generation system 304, multidimensional image reconstruction module 306, window generation module 308, fusion module 310, multidimensional reconstructed image depth adjustment module 312, multidimensional reconstructed image highlight module 314, and multidimensional reconstructed image filter module 316. Database system 302, multidimensional visualization generation system 304, multidimensional image reconstruction module 306, window generation module 308, fusion module 310, multidimensional reconstructed image depth adjustment module 312, multidimensional reconstructed image highlight module 314, and multidimensional reconstructed image filter module 316 may include software and/or hardware components, such as a field programmable gate array (FPGA) or an application specific integrated circuit (ASIC), which performs certain tasks. Database system 302, multidimensional visualization generation system 304, multidimensional image reconstruction module 306, window generation module 308, fusion module 310, multidimensional reconstructed image depth adjustment module 312, multidimensional reconstructed image highlight module 314, and multidimensional reconstructed image filter module 316 may advantageously be configured to reside on an addressable storage medium and configured to be executed on one or more processors. Thus, database system 302, multidimensional visualization generation system 304, multidimensional image reconstruction module 306, window generation module 308, fusion module 310, multidimensional reconstructed image depth adjustment module 312, multidimensional reconstructed image highlight module 314, and multidimensional reconstructed image filter module 316 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

Database system 302 may include a wide variety of data. For example, database system 302 may include any of the following data: multidimensional visualization data, patient data, multidimensional reconstructed image data, selection data, window data, image data, content data, statistical data, historical data, databases, programs, files, libraries, and/or other data, etc.

Database 302 may receive any of the above-mentioned data from a hospital information system.

In some embodiments, multidimensional visualization generation system 304 generates and displays multidimensional visualizations of at least a portion of a target surgical site. The multidimensional visualizations may include images and/or videos and are preferably in 3D and HD. Multidimensional visualization generation system 304 may generate visualizations using a photosensor. The photosensor may respond to any or all of the wavelengths of light that form the electromagnetic spectrum. Alternatively, the photosensor may be sensitive to a more restricted range of wavelengths including at least one wavelength of light outside of the wavelengths of visible light. Visible light may refer to light having wavelengths corresponding to the visible spectrum, which is that portion of the electromagnetic spectrum where the light has a wavelength ranging from about 380 nanometers (nm) to about 750 nm.

In some embodiments, multidimensional image reconstruction module 306 generates a multidimensional reconstructed image. Multidimensional image reconstruction module 306 preferably generates 3D images using 2D pre-operative or intra-operative image slices of a surgical area of a patient. In some example embodiments, multidimensional image reconstruction module 306 generates 3D images using vector-based or feature based construction to create outlines or boundaries of 3D objects from sequential pre-operative 2D image slices.

In some embodiments, window generation module 308 generates and displays a window. Window generation module 308 may generate and display a window based on selection which corresponds to a portion of the generated multidimensional visualization. In some embodiments, window generation module 308 enables a user to adjust the size of the displayed window.

In some example embodiments, fusion module 310 fuses, merges, blends, joins or integrates a multidimensional reconstructed image with a displayed multidimensional visualization. Fusion module 310 may fuse the multidimensional reconstructed image with a multidimensional visualization based on the orientation or coordinates of the surgical site in the multidimensional visualization. In some embodiments, fusion module 310 fuses the multidimensional reconstructed image with a multidimensional visualization based on pattern matching by identifying 3D features, structures, or objects in the multidimensional visualization with corresponding features, structures, or objects in the multidimensional reconstructed image. In some embodiments, fusion module 310 combines appropriate portions of a video signal of the multidimensional visualization with the selected portion of the multidimensional reconstructed image. In some embodiments, fusion module 310 transmits the video signal of the multidimensional visualization of the surgical site to the display device separately from the multidimensional reconstructed image. In these embodiments, fusion module 310 sends an instruction to the display device to display the multidimensional reconstructed image as a graphic atop the appropriate portion of the multidimensional visualization. The instruction may be sent using an HD multimedia interface ("HDMI") communication protocol. In some embodiments, fusion module 310 combines video of the multidimensional visualization with a multidimensional reconstructed image by adjusting visual properties of the multidimensional visualization so as to make the multidimensional visualization merge or fuse with the multidimensional reconstructed image. Adjusting visual properties of the multidimensional visualization may include: (a) increasing the transparency of a portion of a multidimensional visualization so that a multidimensional reconstructed image replaces that portion of the multidimensional visualization; and (b) adjusting visual properties such as adjusting contrast and focus or applying a spline function around edges or fringes where the multidimensional reconstructed image borders a multidimensional visualization. In some embodiments, an image guidance system ("IGS") device registers the microscope with the patient and places the microscope field of view into the pre-operative imaging scan data passing all of the coordinates to our device via Ethernet connection. In some embodiments, imaging system 12 employs machine vision algorithms to identify a target structure (such as a specially marked screw placed into the bones of the spine). The target structure may be registered intra-operatively using an O-arm or C-arm imaging device. The image data from the O-arm or C-arm can then be communicated into our system and fused with the pre-operative data and the live surgical view.

In some embodiments, multidimensional reconstructed image depth adjustment module 312 receives requests to display a portion of a multidimensional reconstructed image having a certain depth. Multidimensional reconstructed image depth adjustment module 312 may enable a user to increase or decrease the depth of the currently displayed multidimensional reconstructed image.

In some embodiments, multidimensional reconstructed image highlight module 314 highlights certain features or portions of the displayed multidimensional reconstructed image. Such features or portions may include internal anatomical structures such as an aneurysm, a tumor or blood vessels.

In some embodiments, multidimensional reconstructed image filter module 316 filters or enables a user to select and remove certain types of anatomical structures of a multidimensional reconstructed image. For example, in one embodiment, imaging system 12 enables a user to select to view only bone structures, brain tissue, blood vessels, tumors or aneurysms. Such a configuration enables users to focus the multidimensional reconstructed image on desired anatomical structures that are important for a surgery.

Although the above has been shown using imaging system 300, there can be many alternatives, modifications, and variations. For example, some of the modules of the imaging system may be expanded and/or combined. Further, in some example embodiments, the functions provided by certain modules may be employed by a separate imaging system operated by a separate entity. In one example, imaging system 300 does not include database system 302. In this example, imaging system 300 may be configured to communicate with a separate database system which includes the data described in database system 302 shown in FIG. 3. Other systems may be inserted to those noted above. Depending upon the embodiment, database system 302, multidimensional visualization generation system 304, multidimensional image reconstruction module 306, window generation module 308, fusion module 310, multidimensional reconstructed image depth adjustment module 312, multidimensional reconstructed image highlight module 314, and multidimensional reconstructed image filter module 316 may be replaced. Further details of these systems are found throughout the present specification.

Imaging system 300 may process data received from other devices. For example, another computing device (e.g., a personal computer) may query data from database system 302 for use in a report.

Numerous embodiments are described in the present application, and are presented for illustrative purposes only. The described embodiments are not, and are not intended to be, limiting in any sense. The present disclosure may be widely applicable to numerous embodiments, as is readily apparent from the disclosure. One of ordinary skill in the art will recognize that the disclosure may be practiced with various modifications and alterations, such as structural, logical, software, and electrical modifications. Although particular features of the disclosure may be described with reference to one or more particular embodiments and/or drawings, it should be understood that such features are not limited to usage in the one or more particular embodiments or drawings with reference to which they are described, unless expressly specified otherwise.

Figure 4:
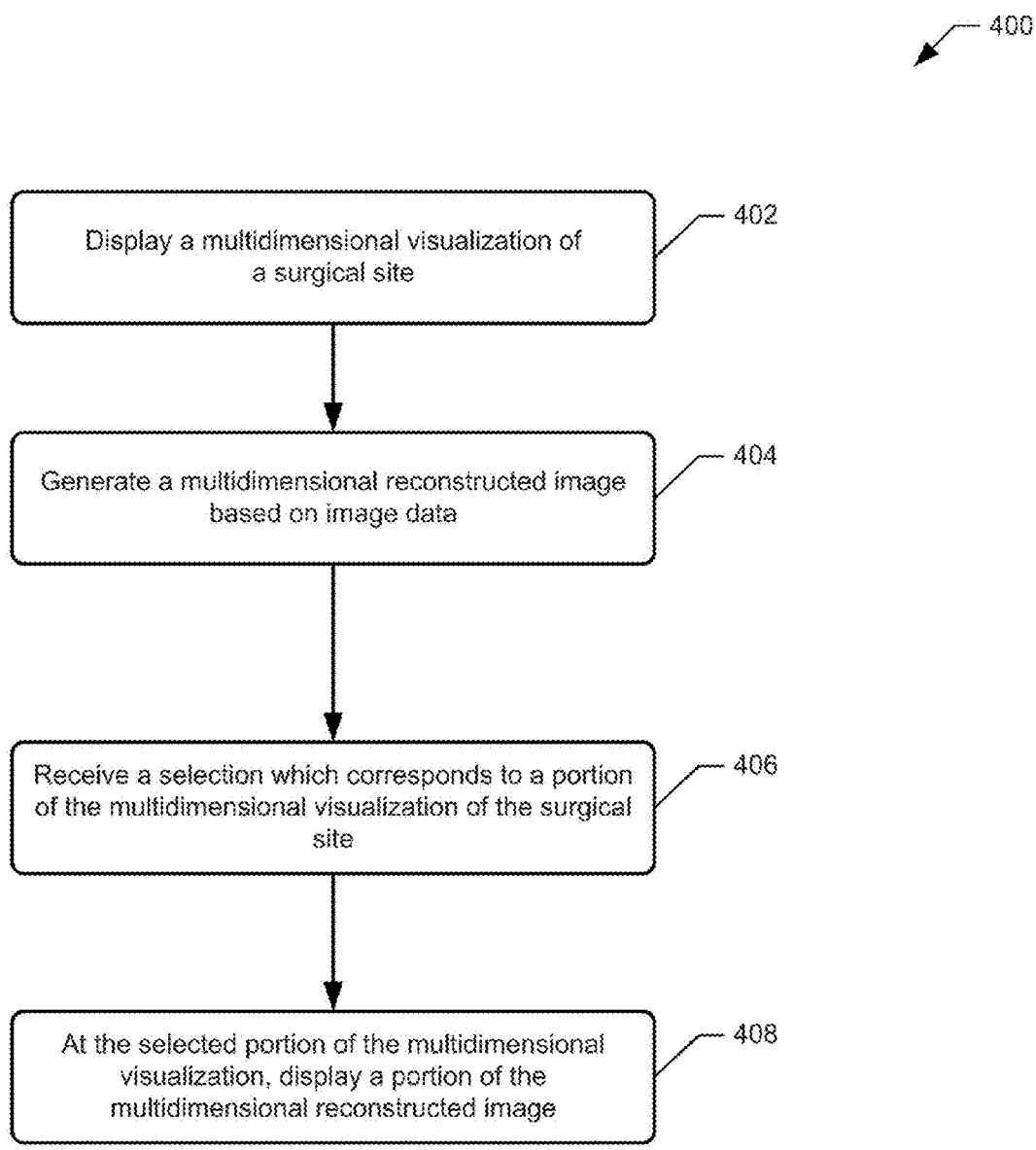
FIG. 4 is a flowchart illustrating an example procedure for displaying a portion of a multidimensional reconstructed image at a selected portion of a multidimensional visualization.

As illustrated in FIG. 4, a flowchart of an example process 400 includes displaying a portion of a multidimensional reconstructed image at a selected portion of a multidimensional visualization of a surgical site. Preferably, process 400 is embodied in one or more software programs which are stored in one or more memories and executed by one or more processors. Although process 400 is described with reference to the flowchart illustrated in FIG. 4, it should be appreciated that many other methods of performing the acts associated with process 400 may be used. For example, the order of the steps may be changed, some of the steps described may be optional, and additional steps may be included.

More specifically, as indicated by block 402, imaging system 12 displays a multidimensional visualization of a surgical site. In some embodiments, imaging system 12 includes a stereoscopic microsurgical visualization system (e.g., a camera or surgical microscope) to capture the multidimensional visualization. The multidimensional visualization is preferably a stereoscopic 3D real time video; however, it may be 2D. The use of a 3D visualization is preferred as it provides many benefits to a surgeon including more effective visualization and depth of field. The multidimensional visualization may be referred to as a real time video.

As indicated by block 404, imaging system 12 may generate a multidimensional reconstructed image based on image data. The image data may be at least one of pre-operative data and intra-operative data. In one example embodiment, imaging system 12 generates a 3D image (or model) based on two-dimensional image slices by determining the sequence of the two-dimensional images, identifying common structures between the images, and forming corresponding three dimensional shapes. Imaging system 12 may generate the multidimensional reconstructed image in real time as visualizations are generated. The multidimensional reconstructed image may be at least one of a 3D multidimensional reconstructed image, a stereoscopic image, and a high definition "HD" image.

As indicated by block 406, imaging system 12 receives a selection which corresponds to a portion of the displayed multidimensional visualization of the surgical site. In one example embodiment, imaging system 12 receives the selection based on a user operating with an input device to select or place a window within a portion of a displayed visualization.

As indicated by block 408, at the selected portion of the multidimensional visualization, imaging system 12 displays a portion of the multidimensional reconstructed image.

Figure 5:
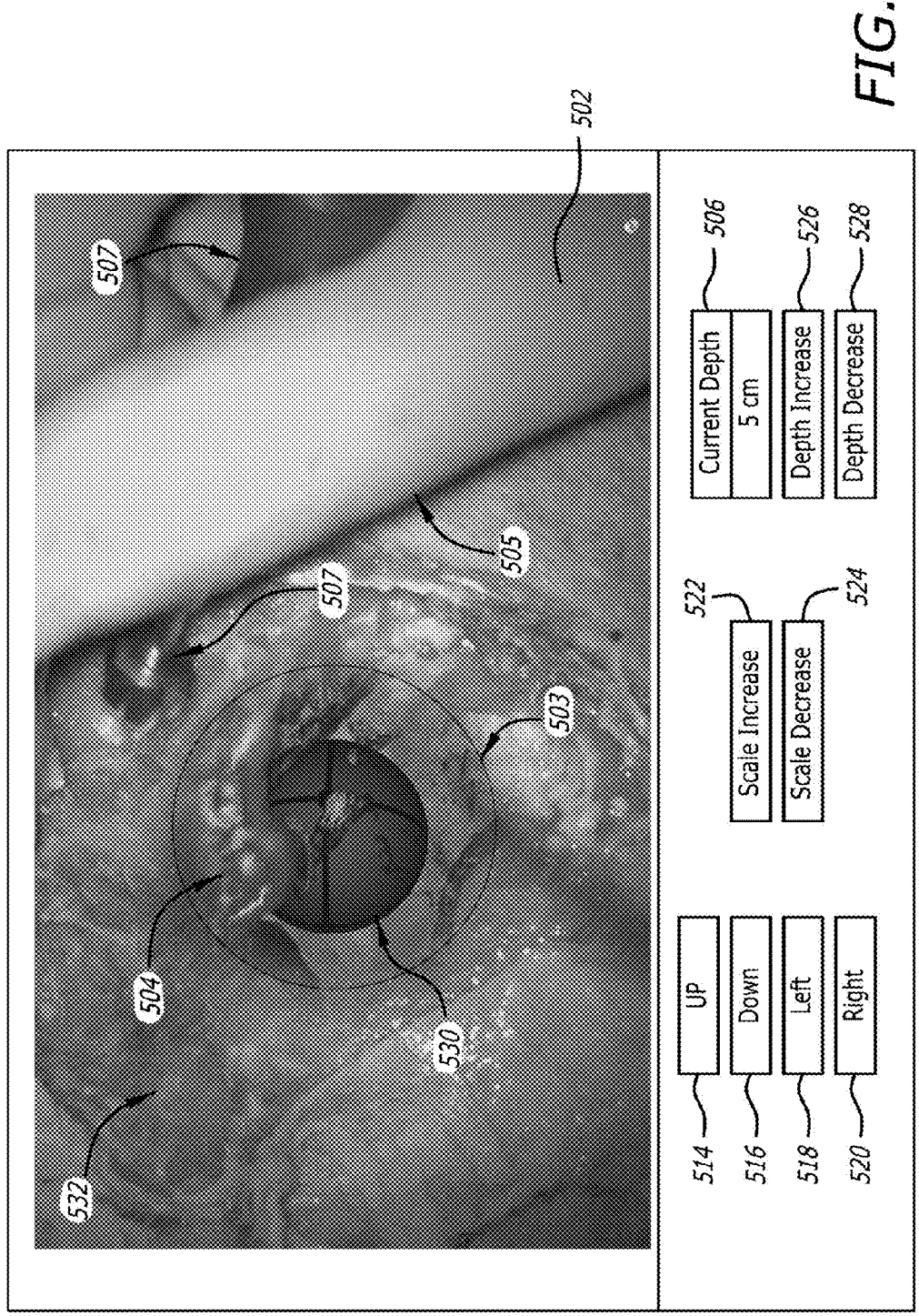
FIG. 5 is a front view of an example imaging system, illustrating a portion of an example multidimensional reconstructed image being fused with a multidimensional visualization of a patient's head.

Referring to FIG. 5, this front view of an example imaging system generally shows an example illustrating a portion of an example multidimensional reconstructed image being fused with a multidimensional visualization of a patient's head. In this embodiment, imaging system 12 highlights a feature (i.e., a brain tumor) of the multidimensional reconstructed image. In this example, surgeon's hand 505 grips cutting tool 507 to cut through the patient's cranium 532. During an operation to remove brain tumor 530, imaging system 12 enables a surgeon to 'see' where tumor 530 is located relative to adjacent patient anatomy and relative to the features of the patient's head shown in visualization 502.

In some embodiments, in response to a second selection which corresponds to a second portion of the visualization, imaging system 12 selects and displays a second portion of the multidimensional reconstructed image at the second selected portion of the visualization.

In some embodiments, imaging system 12 displays a second multidimensional reconstructed image based on a change in a location, size or shape of the window.

In some embodiments, imaging system 12 receives a request selection which corresponds to a different portion of the multidimensional visualization. For example, imaging system 12 may receive a selection based on a user selection of a move button. Referring to FIG. 5, imaging system 12 displays the following move buttons: up button 514, down button 516, left button 518 and right button 520. In response to a user selecting up button 514, imaging system 12 enables the user to cause the position of window 503 to move up relative to the displayed multidimensional visualization 502. It should be appreciated that when window 503 is moved relative to the multidimensional visualization 502, imaging system 12 displays a different portion of the multidimensional reconstructed image. In response to a user selecting down button 516, imaging system 12 enables the user to cause the position of window 503 to move down relative to the displayed multidimensional visualization 502. In response to a user selecting left button 518, imaging system 12 enables the user to cause the position of window 503 to move left relative to the displayed multidimensional visualization 502. In response to a user selecting right button 520, imaging system 12 enables the user to cause the position of window 503 to move right relative to the displayed multidimensional visualization 502.

In some embodiments, in response to a change in the displayed multidimensional visualization, imaging system 12 displays a different portion of the multidimensional reconstructed image that corresponds to the changed multidimensional visualization. Imaging system 12 may determine a change in the visualization has occurred based on at least one of: (a) selections from input device 32; (b) indications from an image guidance system ("IGS") that a surgical microscope has moved; (c) a detected difference between a current visualization and a previous visualization.

In some embodiments, imaging system 12 enables a user to operate with an input device to change the scale of the displayed multidimensional reconstructed image. For example, referring to FIG. 5, in this embodiment, imaging system 12 displays scale increase button 522 and scale decrease button 524. In response to a user selecting scale increase button 522, imaging system 12 enables the user to cause an increase in the display size of at least one of: (a) the displayed multidimensional reconstructed image; and (b) the displayed multidimensional visualization. In response to a user selecting scale decrease button 524, imaging system 12 enables the user to cause a decrease in the display size of at least one of: (a) the displayed multidimensional reconstructed image; and (b) the displayed multidimensional visualization.

In some embodiments, imaging system 12 displays a depth meter that indicates a depth associated with the currently displayed multidimensional reconstructed image. As a result, imaging system 12 enables a user to view relatively deep patient anatomy before the user is able to visually see this anatomy in the displayed multidimensional visualization, via the naked eye, or through optical magnified viewing through a microscope or with surgical loupes. Referring to FIG. 5, in this example, imaging system 12 displays depth meter 506 which indicates a depth coordinate of the currently displayed multidimensional reconstructed image. In this example, depth meter 506 indicates that the currently displayed multidimensional reconstructed image is being displayed at a depth level of 5 cm.

Imaging system 12 also displays depth increase button 526 and depth decrease button 528. In response to a user selecting depth increase button 526, imaging system 12 enables the user to cause an increase in the viewing depth of the currently displayed multidimensional reconstructed image. That is, in response to a user selecting depth increase button 526, imaging system 12 displays a different portion of the multidimensional reconstructed image having an increased depth. In response to a user selecting depth decrease button 528, imaging system 12 enables the user to cause a decrease in the depth of the currently displayed multidimensional reconstructed image. That is, in response to a user selecting depth decrease button 528, imaging system 12 displays a different portion of the multidimensional reconstructed image having a decreased depth.

In some embodiments, imaging system 12 may highlight certain features or portions of the displayed multidimensional reconstructed image. Such features or portions may include internal anatomical structures such as an aneurysm, a tumor or blood vessels. For example, referring to FIG. 5, in this example, imaging system 12 highlights tumor 530. As a result, in this example, imaging system 12 enables a surgeon to 'see' where tumor 530 is located relative to adjacent brain tissue and relative to the features of patient's head shown in visualization 502. Such a configuration allows attention to be brought to important anatomical structures within the multidimensional reconstructed image.

Such features or portions may be highlighted in any suitable way. For example, a tumor may be highlighted with pseudo colors such as purple and blood vessels may be highlighted with a second, different color.

The highlighted anatomy may be manually or automatically selected pre-operatively in the imaging data or selected intra-operatively in the live surgical view based on specific criteria in the image or data. For example, the software may select a specific range of Hounsfield Units or CT densities to identify a tumor or aneurism with calcification as the highlighted anatomy.

In some embodiments, the imaging system inverts the imaging overlay/underlay modality. In typical usage, the "x-ray window" will open up a view that underlays the live surgical view and shows a small portion of the multidimensional reconstruction within the boundaries of the live surgical multidimensional visualization.

Referring to FIG. 5, in this example embodiment, the portion of multidimensional reconstructed image 502 that is displayed within window 503 is displayed as being underlayed with respect to the displayed multidimensional visualization 502. That is, in this example, if the surgeon were to move his thumb 505 over the currently displayed portion of the multidimensional reconstructed image 504, the surgeon's thumb would block the view of the currently displayed multidimensional reconstructed image.

Figure 6:
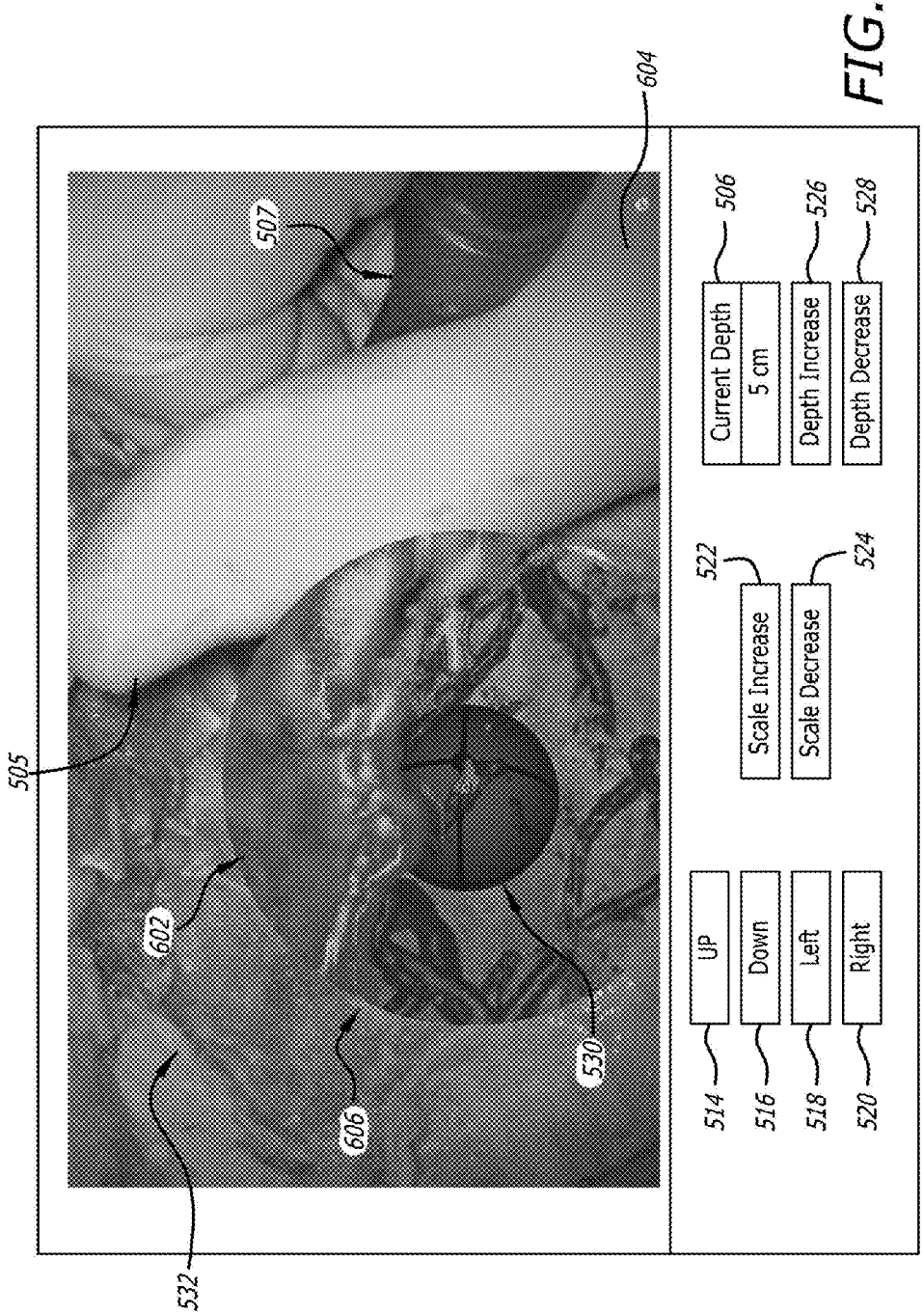
FIGS. 6 and 7 are front views of an example imaging system, illustrating a portion of an example multidimensional reconstructed image being overlayed on a displayed multidimensional visualization of a patient's head.

FIG. 6 illustrates another example embodiment of an imaging system 12, illustrating multidimensional reconstructed image 602 being displayed as being underlayed with respect to the displayed multidimensional visualization 604. That is, the surgeon's thumb blocks the view of the multidimensional reconstructed image 602.

Figure 7:
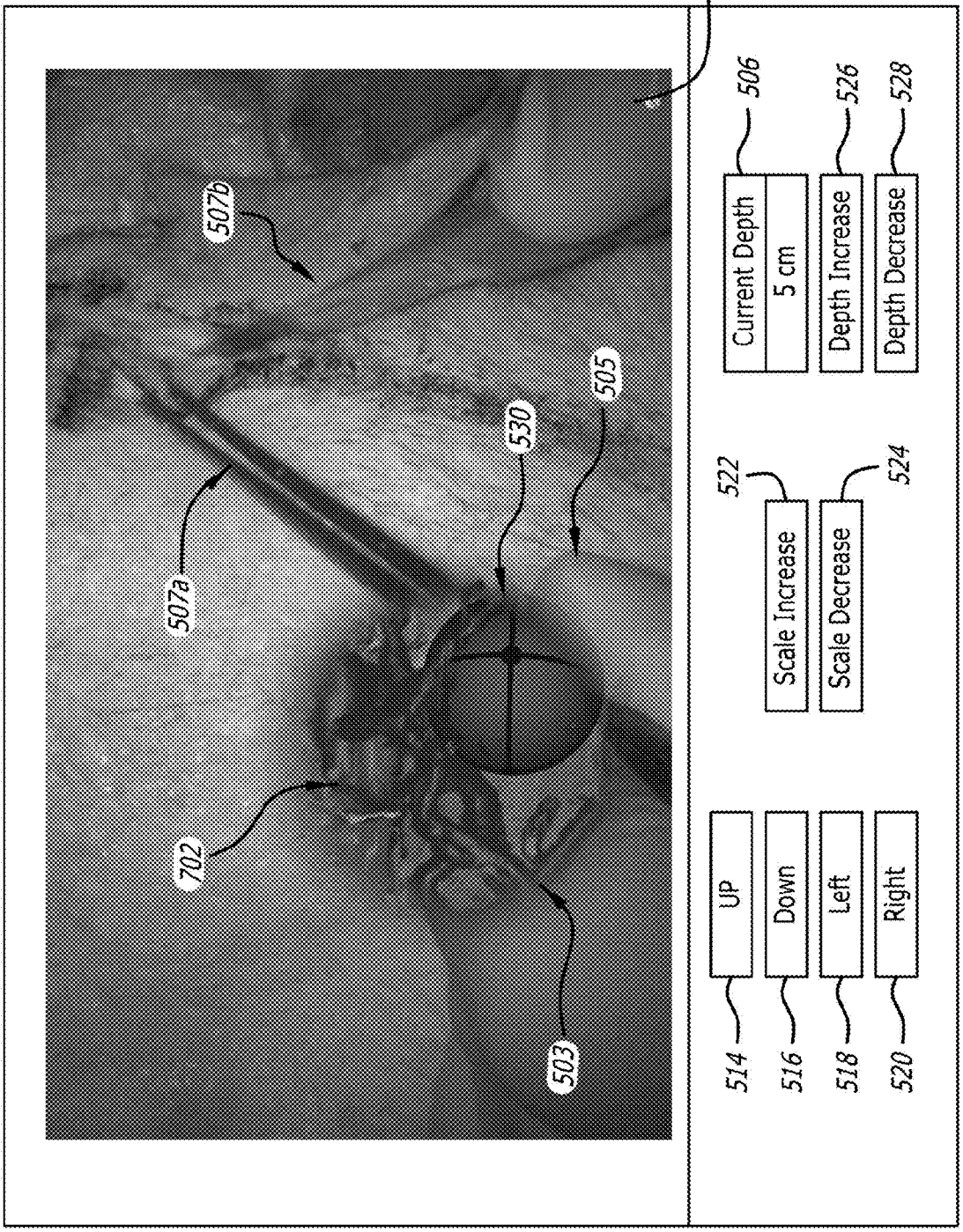

In an alternative embodiment, the portion of multidimensional reconstructed image that is displayed within the window may be displayed as being overlayed with respect to the displayed multidimensional visualization. For example, referring to FIG. 7, the portion of multidimensional reconstructed image 702 is positioned over surgeon's thumb 505 and is shown as being overlayed with respect to multidimensional visualization 704. That is, unlike the multidimensional reconstructed image shown in FIG. 5, the thumb does not block the view of the multidimensional reconstructed image.

Imaging system 12 may fuse or merge the portion of the multidimensional reconstructed image with the multidimensional visualization in any suitable way. In one example embodiment, imaging system 12 fuses the multidimensional reconstructed image with the multidimensional visualization of a target site by using visual tracking and registration of physical features in the multidimensional visualization with the corresponding features in the multidimensional reconstructed image. In another example embodiment, imaging system 12 may orientate a multidimensional reconstructed image with a multidimensional visualization of a surgical site by matching tracking coordinates of the multidimensional visualization with coordinates assigned to the image data. In some embodiments, an image guidance system ("IGS") generates the coordinates. The image guidance system may include the Medtronic® STEALTHSTATION® or BRAINLAB® KOLIBRI™ system. In one example embodiment, imaging system 12 matches identified physical features of a head (e.g., brain bone structure or brain blood vessels) to corresponding features of the multidimensional reconstructed image. In this example, imaging system 12 may match patterns of the blood vessels and brain tissue to the corresponding patterns and features in the multidimensional reconstructed image. In some embodiments, imaging system 12 fuses a portion of the multidimensional reconstructed image based on an orientation of the surgical site shown in the displayed visualization. In some embodiments, imaging system 12 fuses a portion of the multidimensional reconstructed image with a displayed visualization by at least one of the following: (a) adjusting transparencies of the visualization and transparencies of the multidimensional reconstructed image; (b) smoothing borders between the multidimensional reconstructed image and the displayed visualization; and (c) adding the portion of the multidimensional reconstructed image to a video signal with placement determined by an IGS system; (d) analyzing a video signal to determine the location and appearance for placing a portion of the multidimensional reconstruction as a graphical image within the visualization.

In some embodiments, imaging system 12 enables a user to manipulate an input device to change the orientation of the displayed multidimensional reconstructed image. In one example embodiment, imaging system 12 enables a user to click buttons on the screen to move the position of the multidimensional reconstructed image in Cartesian coordinates. In this example, the buttons may be appropriately labeled and enable in and out movement along the x, y, and z axes for position, as well as angular alignment known as roll, pitch, and yaw rotation along the x, y, and z axes. Imaging system 12 may express the position information in any suitable way, such as cylindrical (aka polar) coordinates, spherical (aka radial) coordinates, or other coordinate systems.

In some embodiments, imaging system 12 may enable a user to adjust the multidimensional reconstructed image. For example, in one embodiment, imaging system 12 enables a user to grasp a joystick control (e.g., a LOGITECH® SPACE NAVIGATOR®) to adjust the six degrees of freedom which position multidimensional reconstructed image relative to the multidimensional visualization.

In some embodiments, imaging system 12 enables a user to move a displayed multidimensional reconstructed image based on physical changes to a patient's anatomy made during surgery. For example, a surgeon may move a location of a blood vessel in a multidimensional reconstructed image by selecting and moving the graphical representation of the blood vessel on a display of the multidimensional reconstructed image after a blood vessel has physically been moved in the patient. Such a configuration enables the imaging system to maintain an accurate representation of a patient's anatomical structure during surgery.

In some alternative embodiments, imaging system 12 displays the multidimensional visualization as superimposed onto a portion of the multidimensional reconstructed image. In one example embodiment, a live view of a three inch craniotomy is overlayed onto the overall MRI scan of a patient's head.

In some embodiments, imaging system 12 determines which portion of the multidimensional reconstructed image to display based on coordinates of a selection corresponding to a window. In one example embodiment, imaging system 12 enables a user to generate, place or move a window on the displayed visualization. In this example, imaging system 12 determines which portion of the multidimensional reconstructed image corresponds to the received selection based on the generated window.

In some embodiments, imaging system 12 moves the window in response to a user operating with an input device and clicking and dragging the window.

In some embodiments, imaging system 12 enables a user to draw the shape of the window using input device 32.

In some embodiments, imaging system 12 enables a user to set the window to remain over a specific feature such as a tumor. That is, the window may be 'locked' onto the feature. Such a configuration enables a user to constantly know where the feature is located during a surgery.

In one example embodiment, imaging system 12 enables a user to set the display device to constantly display a designated distance (e.g., ten millimeters) ahead of a currently displayed multidimensional visualization. Such a configuration enables a surgeon to graphically see what anatomical structure his surgical tools are approaching. In this example, as a user moves into a body, imaging system 12 updates the displayed multidimensional reconstructed image to display anatomical structures that are constantly some specified distance ahead.

In some embodiments, imaging system 12 enables surgeons to use a slider or scroll to visually move through different layers or depths of a multidimensional reconstructed image. Such a configuration enables a surgeon to 'view' relatively deep anatomic structures well before a surgeon has physically reached those structures. This configuration also enables a surgeon to functionally slide through different layers to determine what anatomical structure lies between surgical tools and a target anatomy.

In some embodiments, imaging system 12 enables a user to control of the back-side depth of the multidimensional reconstructed image. For example, if a tumor lays close to the cranium, the user may wish to see the full extent of the tumor in the multidimensional reconstruction, but not see the dense bone of the cranium which is just behind the tumor. In this instance, the user can scroll the rear boundary of the multidimensional reconstruction forward until the cranium bone is no longer seen in the multidimensional reconstruction In some embodiments, imaging system 12 automatically displays a portion of a multidimensional reconstructed image having the same depth as the currently displayed multidimensional visualization of a target surgical site.

In some embodiments, imaging system 12 enables a user to cycle through portions of multidimensional reconstructed images until a desired depth is displayed. In some instances, imaging system 12 updates a displayed rendered image as a user scrolls through different depths.

In some embodiments, imaging system 12 enables a user to set which portion of the multidimensional reconstructed image is displayed based on depth information. For example, in one embodiment where a surgeon is cutting into a brain of a patient, imaging system 12 may receive a request from a surgeon to display a 3D reconstructed image corresponding to fifteen mm ahead of where the surgeon's scalpel is currently located. In response to such a request, imaging system 12 may determine coordinates of the currently displayed multidimensional visualization and then display a portion of the multidimensional reconstructed image data that corresponds to fifteen mm ahead of the determined coordinates. In this example, as the surgical tool goes deeper, imaging system 12 automatically updates the displayed portion of the multidimensional reconstructed image to display the portion of the multidimensional reconstructed image that is fifteen mm ahead of surgery.

In one example embodiment, imaging system 12 enables a user to determine the thickness of a multidimensional visualization that is underlaid on a live view. For example, the user may not want to see from fifteen mm ahead all the way to the other side of the cranium. The surgeon may prefer to only see from fifteen mm ahead until they reach the site of the disease state such as an aneurysm. In this case, imaging system 12 may enable the user to select the near and far clipping planes within the multidimensional reconstructed image data.

In some embodiments, imaging system 12 filters or enables a user to select and remove certain types of anatomical structures of a multidimensional reconstructed image. For example, in one embodiment, imaging system 12 enables a user to select to view only bone structures, brain tissue, blood vessels, tumors or aneurisms. Such a configuration enables users to focus the multidimensional reconstructed image on desired anatomical structures that are important for a surgery.

In some embodiments, imaging system 12 adjusts the transparency of a displayed multidimensional reconstructed image so that a highlighted anatomical structure may be viewed through different layers of the multidimensional reconstructed image.

In some embodiments, imaging system 12 enables a user to move or manipulate objects or structure (e.g., a blood vessel or tissue) of a displayed multidimensional reconstructed image to reflect actual movement within a patient's anatomy.

In some embodiments, imaging system 12 displays annotations associated with a multidimensional reconstructed image. In one example embodiment, before surgery a surgeon may electronically attach notations to or in at least one pre-operative image. In this example, imaging system 12 stores the notations and the location of the notation in association with the multidimensional reconstructed image such that the notation is displayed in conjunction with the multidimensional reconstructed image.

In some embodiments, imaging system 12 enables a user to associate a surgical note with a specific portion of image data or a specific portion of a multidimensional reconstructed image. In one example embodiment, in response to a user selecting certain portions of a displayed multidimensional visualization, certain notes which have been associated (e.g., attached) with such selected portions are displayed simultaneously with the displayed portion of the multidimensional reconstructed image.

In some embodiments, imaging system 12 enables a user to draw a route trajectory through a multidimensional reconstructed image or a series of pre-operative images for surgical tools as part of a pre-operative plan. Imaging system 12 may display this route in the displayed portion of the multidimensional reconstructed image in conjunction with a multidimensional visualization of a surgical site.

In some embodiments, imaging system 12 updates which portion of the route is displayed to coincide with the currently displayed multidimensional visualization. As a result, imaging system 12 displays surgical routes in conjunction with a portion of a multidimensional reconstructed image and a multidimensional visualization of a surgical site.

In some embodiments, imaging system 12 may enable a user to control or adjust display characteristics of at least one of the multidimensional reconstructed image and the multidimensional visualization. Display characteristics may include at least one of color, saturation, hue, luminosity, contrast, brightness, gamma and/or any other display characteristics.

The image data may include any suitable type of data. The image data preferably corresponds to a surgical area of a patient. The image data may include at least one of: pre-operative image data; intra-operative image data; scan data; any video, image, or data structure that includes medical information obtained via, for example, a computed tomography ("CT") scan, a computed tomography angiography ("CT-A") scan, a magnetic resonance imaging ("MRI") scan, a positron emission tomography ("PET") scan or any other type of medical scan or imaging; 2D image data; 3D image data; and any sequence or video of medical images that conform to, for example, the Digital Imaging and Communications in Medicine ("DICOM") standard.

The image data may correspond to sequential scans of different depths of a patient's anatomy.

The image data may be generated or received from any suitable device. In some embodiments, the image data is received from a medical imaging machine via a hospital information system. In some embodiments, the image data is received from another server or another computer.

Imaging system 12 may generate the multidimensional reconstructed image based on any suitable method. For example, in one embodiment, imaging system 12 generates a 3D reconstructed image based on image data using vector-based image construction. Vector-based image construction can merge image characteristics of adjacent two-dimensional ("2D") pre-operative medical images into 3D shapes and structures. In another embodiment imaging system 12 generates a 3D reconstructed image based on volumetric image data. Volumetric image data may contain multiple values defining the image at each point in space (known as a voxel). The values at each voxel may include a density (such as Hounsfield units) or other intensity parameter. The filters (defined above) may use this voxel data directly or use a mathematical manipulation of the voxel data such as the gradient of density to define the tissues of interest.

It should be appreciated that the systems and methods disclosed herein may provide an effective guide for a user throughout a surgical procedure. By enabling a user to see a graphical representation of what they are about to cut before they actually cut it, imaging system 12 provides the user with a better idea of where they are going and what they are to avoid in getting there. The configurations disclosed herein enable surgeons to 'view' anatomic structure below a displayed visualization before physically reaching that point. Imaging system 12 provides surgeons a type of 'x-ray' vision into a patent's anatomy in the form of a multidimensional reconstructed image being displayed to appear as being fused with a real time multidimensional visualization. In other words, such a configuration provides surgeons with a type of x-ray vision to 'see' varying layers of a patient's anatomy in relation to a currently displayed multidimensional visualization without actually having to physically expose those layers.

It should be appreciated that, in some embodiments, the systems and methods disclosed herein may enable a surgeon to comfortably visualize a surgical procedure on a display device instead of staring for, in some cases, several hours though the eyepieces of a surgical microscope. This is because the real-time visualizations of the systems and methods allow the surgery to take place in comfortable sitting or standing positions without sacrificing a complete and accurate visualization of the target surgical field. Traditionally the primary surgeon and any assistant surgeons have to be physically looking through the microscope oculars—positioning themselves in rigid and frequently awkward positions. By viewing the surgery on a display, a surgeon is free to sit comfortably and easily move their necks, backs, and shoulders to remain relaxed and ergonomically situated. These capacities may be ideal for a surgeon and surgical team working long hours. Working such long hours under bright lights that generate intense heat in order to visualize the target surgical area, as is commonly the case in many known surgical procedures, may result in previously unavoidable surgeon discomfort and fatigue. Additionally, it is not uncommon for a surgeon to be wearing several layers of clothing along with surgical barriers, including gloves, face barriers, goggles, hats, and overcoats, to name a few, during a given surgical procedure, further contributing to discomfort and fatigue. Similarly, it is not uncommon for a surgeon to look away from a target surgical site in order to change or to move equipment, glance at other equipment such as IGS and/or patient vital sign monitors, to take a mental break, or to communicate with a surgical team or students. Upon looking back onto the traditional target surgical site, the surgeon would have to wait briefly to allow his eyes to adjust to the normal high intensity lighting in the eyepieces, causing delays in the procedure. The systems and methods of the present invention may eliminate this problem by providing a display which fits into the normal visual filed of the surgeon.

Even further still, the systems and methods described herein allow a surgical team to position themselves in the most appropriate location for the surgery, not necessarily where the shadows dictate. Moreover, the systems and methods provide an ideal environment for students to observe a procedure in comfortable positions especially when used with multiple screens or with a large display such as a projection screen.

Thus, imaging system 12 provides multidimensional internal guidance rather than just surface guidance. As a result, imaging system 12 may reduce surgery time, reduce trauma from surgery, and may provide better surgery with fewer complications. In addition, the imaging system may eliminate a need for some visualization probes or cameras in delicate or hard to reach areas.

In some embodiments, the imaging system 12 is a single device. In some embodiments, imaging system 12 is configured to be retrofitted onto existing surgical equipment such as surgical microscopes or an open surgery apparatus. This can be advantageous as the retrofit embodiments may be added to existing systems (e.g., microscopes and IGS), allowing expensive equipment to simply be upgraded as opposed to purchasing an entirely new system. An example imaging system 12 may include various optical or electronic magnification systems including stereomicroscopes or may function as an open surgery apparatus utilizing cameras and overhead visualizations with or without magnification.

Figure 8:
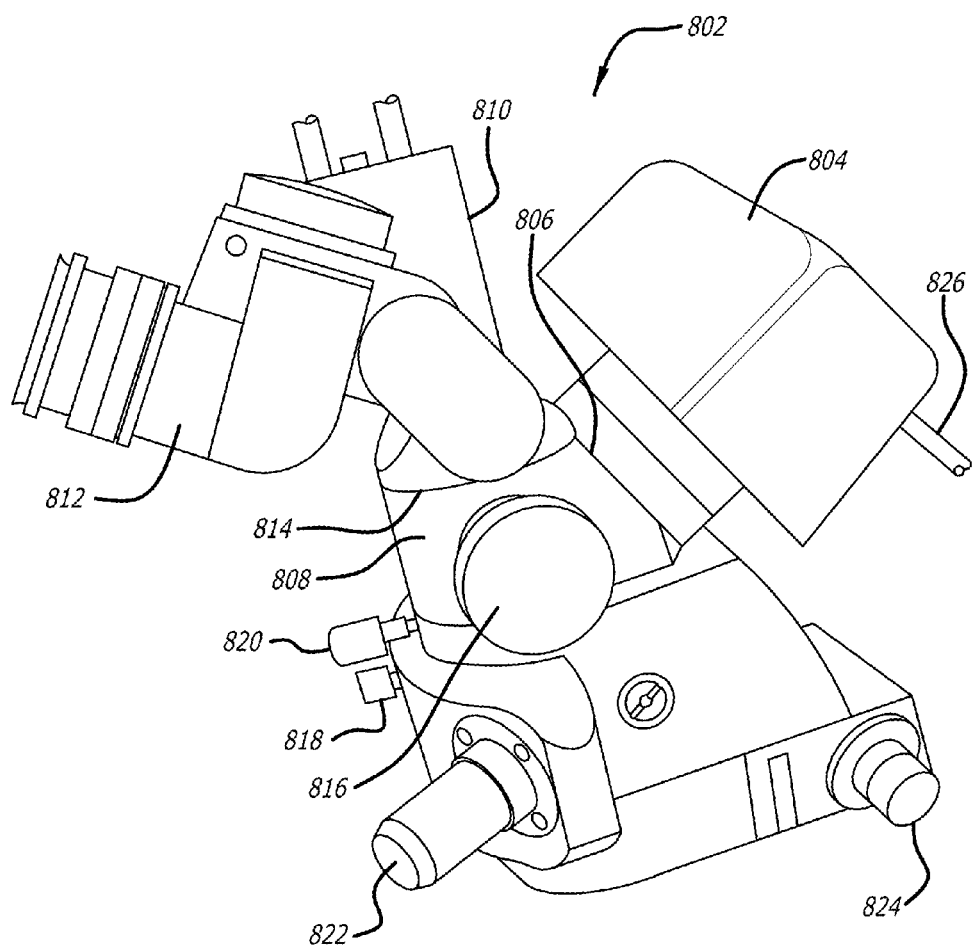
FIG. 8 is perspective view of an example imaging system, illustrating the imaging system being retrofitted onto a surgical device.

FIG. 8 illustrates an example embodiment in which an example imaging system is retrofitted onto a surgical microscope. More specifically, surgical microscope 802 is retrofitted with imaging system 804. In this example embodiment, imaging system 804 is coupled to first ocular port 806 on ocular bridge 808. Further, ocular bridge 808 couples video camera 810 to a second ocular port (not shown) and binocular eyepiece 812 to third ocular port 814. Forth ocular port 816 is available for further retrofits to surgical microscope 802. Although surgical microscope 802 has been retrofitted with imaging system 804, it still retains the use of conventional controls and features such as, but not limited to, iris adjustment knob 818, first adjustment knob 820, second adjustment knob 822, illumination control knob 824, and an objective lens (not shown). Further still, imaging system 804 may send and receive information through signal cable 826.

The imaging system, imaging apparatuses and imaging methods of the present invention may be applicable to any form of surgery, such as brain surgery, spinal surgery, ophthalmologic surgery, corneal transplants, neurosurgery, orthopedic surgery, ear, nose and throat surgery, plastics and reconstructive surgery, or general surgery on any target structure or tissue.

As discussed above, in some embodiments, touch screen systems may be used to manipulate images and reconstructions. In some embodiments, imaging system 12 enables a user to operate with an input device (e.g., a 3D mouse such as the SPACE NAVIGATOR®) to position templates, images, and references within the multidimensional reconstructed image. In some embodiments, imaging system 12 includes a foot switch or a lever for positioning templates, images, and references. Such a configuration enables a user to manipulate multidimensional reconstructed images without taking his or her eyes off of a visualization of a surgical procedure, enhancing performance and safety.

In some embodiments, imaging system 12 includes a voice activated control system. Such a configuration enables a user to control the modification and alignment of multidimensional reconstructed images in conjunction with a multidimensional visualization of a surgical site as if he or she was talking to an assistant or a member of the surgical team. The voice activated controls may include a microphone and a second data processor or software to interpret the oral voice commands.

In some embodiments, imaging system 12 includes a gesture recognition device configured to enable a user to use gesture commands to control multidimensional reconstructed images fused with a visualization of a surgical site. The gesture recognition device may include a camera to monitor and track the gestures of the controlling user and, optionally, a second data processor or software to interpret the commands.

In some embodiments, imaging system 12 implements camera calibration on one or more photosensors to identify the parameters typically used for image rectification, camera principal points including: (a) position in x,y,z; (b) rotational orientation in angles phi, theta, psi; (c) focal length and magnification/field of view; and (d) distortion parameters which may characterize optical aberrations including any or all of the following: defocus, piston, tilt, shear, astigmatism, coma, or other higher order aberrations or chromatic aberrations. Once characterized, imaging system 12 may apply corrections to the video signal which results in an orthoscopic or rectilinear visualization of the surgery.

In some embodiments, imaging system 12 employs camera calibration parameters to apply the optical distortion that is present in the video signal to the reconstruction such that the final rendering of the pre-operative data reflects the same distortion and aberrations present in the video signal. By matching the lighting, geometry, and distortion parameters between the live video signal and the 3D reconstruction, the graphical multidimensional reconstructed image will most precisely match the live view of the surgical sight and provide the surgeon with the most accurate navigational guidance during the procedure.

Figure 9:
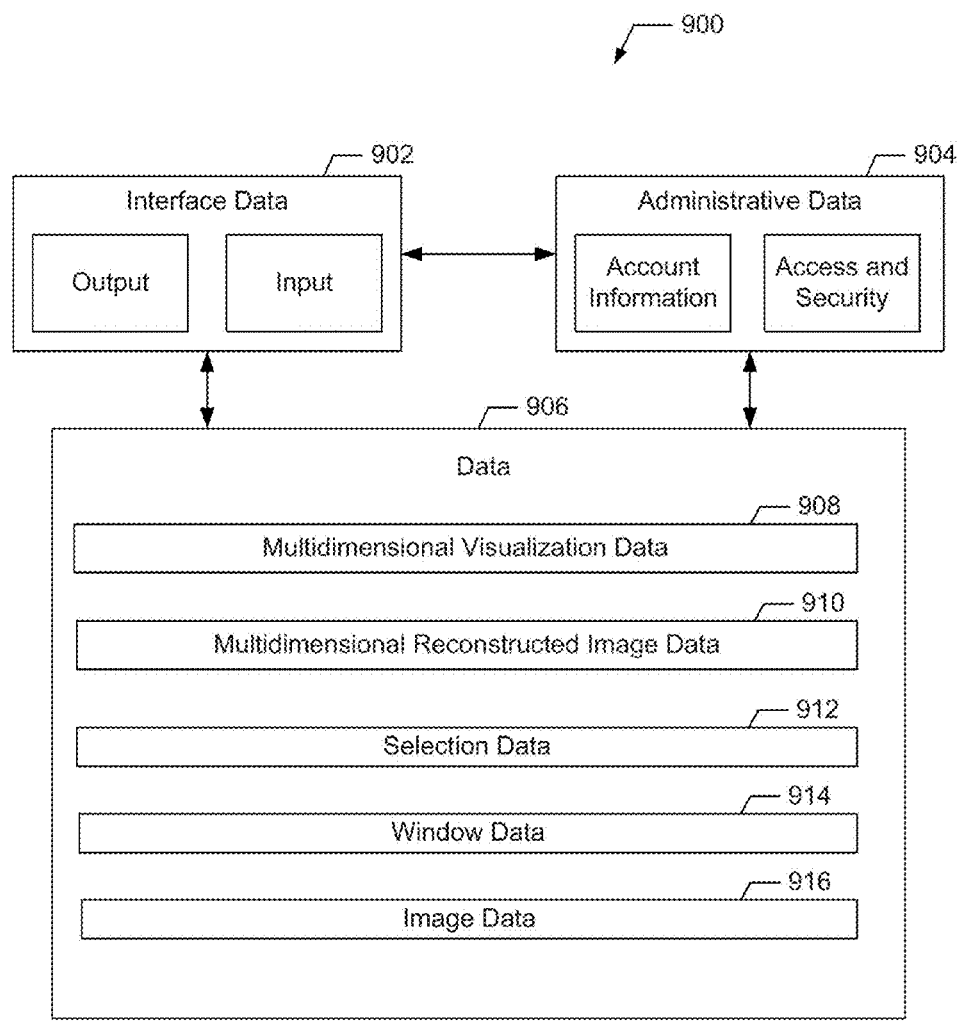
FIG. 9 is a block diagram showing an example data architecture, according to an example embodiment of the imaging system disclosed herein.

FIG. 9 is a block diagram of an example data architecture 900. In this example embodiment, interface data 902, administrative data 904, and data 906 interact with each other, for example, based on user commands or requests. Interface data 902, administrative data 904, and data 906 may be stored on any suitable storage medium (e.g., database system 302 and/or server 14). It should be appreciated that different types of data may use different data formats, storage mechanisms, etc. Further, various applications may be associated with processing interface data 902, administrative data 904, and data 906. Various other or different types of data may be included in the example data architecture 900.

Interface data 902 may include input and output data of various kinds. For example, input data may include mouse click data, scrolling data, hover data, keyboard data, touch screen data, voice recognition data, etc., while output data may include image data, text data, video data, audio data, etc. Interface data 902 may include formatting, user interface options, links or access to other websites or applications, and the like. Interface data 902 may include applications used to provide or monitor interface activities and handle input and output data.

Administrative data 904 may include data and applications regarding user accounts. For example, administrative data 904 may include information used for updating accounts, such as creating or modifying user accounts and/or host accounts. Further, administrative data 904 may include access data and/or security data. Administrative data 904 may include a terms of service agreement. Administrative data 904 may interact with interface data 902 in various manners, providing interface data 902 with administrative features, such as implementing a user login and the like.

Data 906 may include, for example, multidimensional visualization data 908, multidimensional reconstructed image data 910, selection data 912, window data 914, and image data 916.

Multidimensional visualization data 908 may include data representative of at least one of: a surgical site, a 3D visualization of a surgical site, a 2D visualization of a surgical site, and real time data.

Multidimensional reconstructed image data 910 may include data representative of at least one of: feature data, brain tumor data, brain tissue data, bone structure data, aneurysm data, blood vessel data, vertebrate data, coordinate data, depth data, distance data, and transparency data.

Selection data 912 may include data representative of at least one of: a portion of a multidimensional visualization.

Window data 914 may include data representative of position data.

Image data 916 may include data representative of at least one of: pre-operative image data, intra operative image data, medical scan data, and image slice data.

The imaging system may include components of Applicant's TrueVision Systems, Inc. real-time 3D HD visualization systems described in Applicant's co-pending U.S. application Ser. No. 11/256,497 entitled "Stereoscopic Image Acquisition Device," filed Oct. 21, 2005; Ser. No. 11/668,400 entitled "Stereoscopic Electronic Microscope Workstation," filed Jan. 29, 2007; Ser. No. 11/668,420 entitled "Stereoscopic Electronic Microscope Workstation," filed Jan. 29, 2007; Ser. No. 11/739,042 entitled "Stereoscopic Display Cart and System," filed Apr. 23, 2007; and Ser. No. 61/042,606, entitled "Apparatus and Methods for Performing Enhanced Visually Directed Procedures Under Low Ambient Light Conditions," filed Apr. 4, 2008, all of which are fully incorporated herein by reference as if part of this specification.

"Realtime" as used herein generally refers to the updating of information at essentially the same rate as the data is received. More specifically, "realtime" is intended to mean that the image data is acquired, processed, and transmitted from the photosensor of the visualization generation system at a high enough data rate and at a low enough time delay that when the data is displayed, objects presented in the visualization move smoothly without user-noticeable judder, latency or lag. Typically, this occurs when new images are acquired, processed, and transmitted at a rate of at least about 30 frames per second ("fps") and displayed at a rate of at least about 60 fps and when the combined processing of the video signal has no more than about $\frac{1}{10}^{th}$ of a second of delay.

In some embodiments, new images are acquired, processed, and transmitted at a rate of at least about 24 fps, about 30 fps, about 35 fps, about 40 fps, about 50 fps, about 60 fps, about 70 fps, about 80 fps, about 90 fps or about 120 fps. Also, new images are displayed at a rate of at least about 60 fps, about 70 fps, about 80 fps, about 90 fps or about 120 fps. The signal processing may have no more than about $1/20^{th}$ second of delay, about $1/30^{th}$ second of delay, about $1/50^{th}$ second of delay, about $1/90^{th}$ second of delay, about $1/120^{th}$ second of delay, about $1/500^{th}$ second of delay, or about $1/1000^{th}$ second delay or more.

The term "high definition" or "HD" as used herein may encompass a video signal having a resolution of at least 960 lines by 720 lines and to generally have a higher resolution than a standard definition (SD) video. For purposes of the present disclosure, this may be accomplished with display resolutions of 1280 lines by 720 lines (720p and 720i) or 1920 lines by 1080 lines (1080p or 1080i). In contrast, standard definition (SD) video typically has a resolution of 640 lines by 480 lines (480i or 480p) or less. It is however, within the scope of the present disclosure that the multidimensional visualization may be in SD, though HD is preferred. Further implementations using 4 k displays with a resolution up to 4096 by 2160, 8 k displays with a resolution up to 7680 by 4320 are within the scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that at least one member of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventors expect skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. An imaging system comprising:
   at least one photosensor configured to record a visualization of a surgical site;
   a visualization generation system configured to create a multidimensional visualization based on the recorded visualization of the surgical site;
   a processor communicatively coupled to a display device, the processor configured to display the multidimensional visualization of the surgical site;
   an image reconstruction module configured to
      receive a selection corresponding to a portion of the displayed multidimensional visualization of the surgical site,
      create a reconstructed image related to the surgical site, and
      select a portion of the reconstructed image that corresponds to the selected portion of the multidimensional visualization; and
   a fusion module configured to combine the portion of the reconstructed image with the multidimensional visualization, wherein the processor is configured to display the portion of the reconstructed image in addition to the multidimensional visualization.

2. The imaging system of claim 1, wherein the reconstructed image is created from at least one of a two-dimensional pre-operative image, a three-dimensional pre-operative image, and at least one intra-operative image slice of the surgical site.

3. The imaging system of claim 1, wherein the image reconstruction module is configured to create the reconstructed image as a three-dimensional reconstructed image using vector-based or feature based construction to create outlines of objects located within sequential pre-operative image slices.

4. The imaging system of claim 1, wherein the fusion module is configured to at least one of fuse, merge, blend, join, and integrate the portion of the reconstructed image with the multidimensional visualization at the selected portion of the multidimensional visualization.

5. The imaging system of claim 1, wherein the fusion module is configured to select the portion of the reconstructed image by:
  determining at least one of an orientation and coordinates of the selected portion of the multidimensional visualization;
  determining at least one of a corresponding orientation and coordinates of the reconstructed image; and
  selecting the portion of the reconstructed image that is associated with the at least one of the corresponding orientation and coordinates.

6. The imaging system of claim 1, wherein the fusion module is configured to combine the portion of the reconstructed image with the multidimensional visualization by:
  identifying at least one of a feature, a structure, and an object inside of or within proximity of the selected portion of the multidimensional visualization;
  identifying at least one of a corresponding feature, structure, and object within the reconstructed image; and
  aligning the portion of the reconstructed image with the selected portion of the multidimensional visualization such that the at least one identified feature, structure, and object of the multidimensional visualization is aligned with the at least one corresponding identified feature, structure, and object of the reconstructed image.

7. The imaging system of claim 6, wherein at least one of the feature, structure, and object includes at least one of brain tissue, a blood vessel, a tumor, bone tissue, muscle tissue, and a marker.

8. An imaging apparatus comprising:
  a visualization generation system configured to create a multidimensional visualization based on a recorded visualization of a surgical site;
  a processor communicatively coupled to a display device, the processor configured to display the multidimensional visualization of the surgical site;
  an image reconstruction module configured to
    receive a selection corresponding to a portion of the displayed multidimensional visualization of the surgical site,
    create a reconstructed image related to the surgical site, and
    select a portion of the reconstructed image that corresponds to the selected portion of the multidimensional visualization; and
  a fusion module configured to combine the portion of the reconstructed image with the multidimensional visualization,
  wherein the processor is configured to display the portion of the reconstructed image in addition to the multidimensional visualization.

9. The imaging apparatus of claim 8, wherein the fusion module is configured to combine the portion of the reconstructed image with the multidimensional visualization by integrating, within a video signal, the portion of the reconstructed image with the multidimensional visualization at the selected portion.

10. The imaging apparatus of claim 8, wherein the processor is configured to transmit, to the display device, the multidimensional visualization separately from the portion of the reconstructed image.

11. The imaging apparatus of claim 10, wherein the processor is configured to transmit an instruction to the display device specifying a location of the selected portion of the multidimensional visualization to which the portion of the reconstructed image is to be superimposed as a graphic.

12. The imaging apparatus of claim 8, wherein the fusion module is configured to combine the multidimensional visualization with the portion of the reconstructed image by adjusting a visual property of at least one of the multidimensional visualization and the portion of the reconstructed image so as to make the multidimensional visualization merge or fuse with the portion of the reconstructed image.

13. The imaging apparatus of claim 12, wherein the fusion module is configured to adjust the visual property by at least one of:
  (a) increasing a transparency of the selected portion of the multidimensional visualization so that the portion of the reconstructed image replaces the selected portion of the multidimensional visualization;
  (b) adjusting a contrast around edges or fringes of at least one of the selected portion of the multidimensional visualization and the portion of the reconstructed image;
  (c) adjusting a focus around edges or fringes of at least one of the selected portion of the multidimensional visualization and the portion of the reconstructed image; and
  (d) applying a spline function around edges or fringes of at least one of the selected portion of the multidimensional visualization and the portion of the reconstructed image.

14. The imaging apparatus of claim 8, wherein the fusion module is configured to combine the portion of the reconstructed image with the multidimensional visualization by:
  identifying a target structure within the multidimensional visualization;
  identifying the same target structure within the reconstructed image;
  aligning the reconstructed image with the multidimensional visualization such that the target structure within the multidimensional visualization is aligned with the target structure within the reconstructed image; and
  identifying the portion of the reconstructed image that is located at a same location as the selected portion of the multidimensional visualization.

15. The imaging apparatus of claim 14, wherein the target structure includes a marked screw and is registered intraoperatively using an O-arm or C-arm imaging device.

16. An imaging method comprising:
  creating, via a processor, a multidimensional visualization based on a recorded visualization of a surgical site;

creating, via the processor, a reconstructed image related to the surgical site;

displaying, via the processor in a display device, the multidimensional visualization of the surgical site, receiving, via the processor from an input device, a selection of a portion of the displayed multidimensional visualization;

selecting, via the processor, a portion of the reconstructed image that corresponds to the selected portion of the multidimensional visualization;

combining, via the processor, the portion of the reconstructed image with the multidimensional visualization; and displaying, via the processor in the display device, the portion of the reconstructed image in addition to the multidimensional visualization.

17. The imaging method of claim 16, wherein the selected portion of the multidimensional visualization is represented as a window.

18. The imaging method of claim 17, further comprising:

receiving, via the processor from the input device, an instruction to move a position of the window in response to the window being clicked and dragged;

determining a second portion of the displayed multidimensional visualization based on the moved position of the window;

selecting, via the processor, a second portion of the reconstructed image that corresponds to the second portion of the multidimensional visualization;

combining, via the processor, the second portion of the reconstructed image with the multidimensional visualization; and displaying, via the processor in the display device, the second portion of the reconstructed image in addition to the multidimensional visualization.

19. The imaging method of claim 16, wherein combining the portion of the reconstructed image with the multidimensional visualization includes fusing the portion of the reconstructed image by identifying first features of the multidimensional visualization and aligning the first features to correspond to second features of the reconstructed image.

20. The imaging method of claim 16, wherein combining the portion of the reconstructed image with the multidimensional visualization includes at least one of:

increasing a transparency of the selected portion of the multidimensional visualization; and applying a smoothing function to a boundary between the portion of the reconstructed image and the multidimensional visualization.

* * * * *